US005986079A

United States Patent [19]
Barr et al.

[11] Patent Number: 5,986,079
[45] Date of Patent: *Nov. 16, 1999

[54] EXPRESSION OF PACE IN HOST CELLS AND METHODS OF USE THEREOF

[75] Inventors: Philip J. Barr; Anthony J. Brake, both of Berkeley, Calif.; Randal J. Kaufman, Boston, Mass.; Patricia Tekamp-Olson, San Anselmo, Calif.; Louise Wasley, Medfield, Mass.; Polly A. Wong, Mountain View, Calif.

[73] Assignees: Genetics Institute, Inc., Cambridge, Mass.; Chiron Corporation, Emeryville, Calif.

[ * ] Notice: This patent is subject to a terminal disclaimer.

[21] Appl. No.: 08/480,382

[22] Filed: Jun. 7, 1995

Related U.S. Application Data

[60] Division of application No. 07/885,972, May 20, 1992, Pat. No. 5,460,950, which is a continuation-in-part of application No. 07/621,092, Nov. 26, 1990, abandoned, application No. 07/620,859, Nov. 29, 1990, abandoned, application No. 07/621,443, Nov. 29, 1990, abandoned, and application No. 07/621,457, Nov. 30, 1990, abandoned.

[51] Int. Cl.$^6$ .......................... C12N 15/57; C12N 15/79; C12N 15/85; C12N 9/64
[52] U.S. Cl. .................. 536/23.2; 435/69.1; 435/219; 435/226; 435/252.3; 435/320.1; 435/471; 536/23.5
[58] Field of Search ..................... 435/219, 226, 435/240.1, 243, 252.3, 69.1, 69.6, 69.8, 71.1, 320.1, 471; 530/350, 381, 383, 384; 536/23.2, 23.5

[56] References Cited

U.S. PATENT DOCUMENTS

| | | |
|---|---|---|
| 4,652,639 | 3/1987 | Stabinsky . |
| 4,703,008 | 10/1987 | Lin ........................................ 435/240.2 |
| 4,745,051 | 5/1988 | Smith et al. . |
| 4,770,999 | 9/1988 | Kaufman et al. .......................... 435/68 |
| 4,784,950 | 11/1988 | Hagen et al. ............................. 435/68 |
| 4,870,023 | 9/1989 | Fraser et al. ............................. 435/320 |
| 4,929,553 | 5/1990 | Bussey et al. ....................... 435/172.3 |
| 4,992,373 | 2/1991 | Bang et al. ............................. 435/226 |
| 5,004,803 | 4/1991 | Kaufman et al. ....................... 530/383 |
| 5,041,378 | 8/1991 | Drummond et al. ................... 435/234 |
| 5,059,528 | 10/1991 | Bollen et al. .......................... 435/69.4 |
| 5,077,204 | 12/1991 | Brake et al. ............................ 435/68.1 |
| 5,460,950 | 10/1995 | Barr et al. .............................. 435/69.1 |
| 5,741,664 | 4/1998 | Ballinger et al. ....................... 435/68.1 |

FOREIGN PATENT DOCUMENTS

| | | |
|---|---|---|
| 246709 | 11/1987 | European Pat. Off. . |
| 319944 | 6/1989 | European Pat. Off. . |
| 0327377 | 8/1989 | European Pat. Off. . |
| WO89/09220 | 10/1989 | WIPO . |
| WO91/06314 | 5/1991 | WIPO . |
| WO92/09698 | 6/1992 | WIPO . |

OTHER PUBLICATIONS

Sergeev et al. (1992) Bioc. Biop. Res. Comm. 189:1543–1547 "Vitamin K–Dependent γ–carboxylation of the 1,25–Dihydroxyvitamin $D_3$ Receptor".

P. Bresnahan et al, "Expression and Initial Characterization of Furin: A Human Endoprotease Capable of Cleaving Pro–β–NGF in vivo", *J. Cell Biol.*, 111:228a (Dec. 1990) Abstract #1275.

R. Kaufman et al, "Factors Limiting Expression of Secreted Protein sin Mammalian Cells", in Proceedings of the American Red Cross Twenty–first Annual Scientific Symposium: Impact of Recombinant Technology in Hemostasis and Thrombosis, ed. L. W. Hoyer at al, Plenum Press, New York (May, 1990).

Printout of EMBL Database Entry X15723.

R. Kaufman et al, "Expression, Purification, and Characterization of Recombinant y–Carboxylated Factor IX Synthesized in Chinese Hamster Ovary Cells", *J. Biol. Chem.*, 261(21):9622–9628 (Jul. 25, 1986) [Kaufman I].

R. Kaufman et al, "Rate Limiting Steps in the Synthesis and Secretion of Heterologous Proteins in Mammalian Cells", *The Proceedings of the Fifth European Congress of Biotechnology*, eds. Christiansen, Munck, Villadsen, vol. 2, Munksgaard Int. Publ. Copenhagen, pp. 715–719 (1990) [Kaufman II].

R. Kaufman et al, "Improved Vectors for Stable Expression of Foreign Genes in Mammalian Cells by Use of the Untranslated Leader Sequence from EMC Virus", *Nucl. Acids Res.*, 19(16):4485–4490 (Aug. 25, 1991) [Kaufman III].

R. Kaufman, "Selection and Coamplification of Heterologous Genes in Mammalian Cells", *Meth. Enzymol.*, 185:537–566 (Jun. 5, 1990) [Kaufman IV].

R. Kaufman et al, "The Phosphorylation State of Eucaryotic Initiation Factor 2 Alters Translational Efficiency of Specific mRNAs", *Mol. Cell. Biol.*, 9(3):946–958 (Mar. 1989) [Kaufman V].

R. Kaufman et al, "Translational Efficiency of Polycistronic mRNAs and Their Utilization to Express Heterologous Genes in Mammalian Cells", *EMBO J.*, 6(1):187–193 (1987) [Kaufman VI].

A. van den Ouweland et al, "Structural Homology Between the Human fur Gene Product and the Subtilisin–like Protease Encoded by Yeast KEX2", *Nucl. Acids. Res.*, 18(3):664 (Feb., 1990) [van den Ouweland I].

(List continued on next page.)

*Primary Examiner*—Ponnathapura Achutamurthy
*Assistant Examiner*—William W. Moore
*Attorney, Agent, or Firm*—Howson and Howson

[57] ABSTRACT

Compositions and methods are provided for endopeptidase production and for enhanced efficiencies of processing heterologous precursor polypeptides to mature polypeptides, including proteins requiring gamma-carboxylation for biological activity. These compositions and methods utilize recombinant PACE, a mammalian endopeptidase that is specific for dibasic amino acid sites.

7 Claims, 12 Drawing Sheets

OTHER PUBLICATIONS

A. van den Ouweland et al, "Nucleotide Sequence Analysis of the Human fur Gene", *Nucl. Acids Res.*, 17(17):7101–7102 (Sep. 12, 1989) [van den Ouweland II].

D. Julius et al, "Isolation of the Putative Structural Gene for the Lysine–Arginine–Cleaving Endopeptidase Required for Processing of Yeast Prepro–a–Factor", *Cell*, 37:1075–1089 (Jul., 1984) [Julius I].

D. Julius et al, "Glycosylation and Processing of Prepro–a–Factor Through the Yeast Secretory Pathway", *Cell*, 36:309–318 (Feb., 1984) [Julius II].

R. Fuller et al, "Yeast Prohormone Processing Enzyme (KEX2 Gene Product) is a Ca2+–dependent Serine Protease", *Proc. Natl. Acad. Sci. USA*, 86:1434–1438 (Mar., 1989) [Fuller I].

R. Fuller et al, "Intracellular Targeting and Structural Conservation of a Prohormone–Processing Endoprotease", *Science*, 246:482–486 (Oct. 27, 1989) [Fuller II].

R. Fuller et al, "The *Saccharomyces cerevisiae* KEX2 Gene, Required for Processing Prepro–a–Factor, Encodes a Calcium–Dependent Endopeptidase that Cleaves after Lys–Arg and Arg–Arg Sequences", *Microbiology*, pp. 273–278 (1986) [Fuller III].

A. Roebroek et al, "Evolutionary Conserved Close Linkage of the c–fes/fps Proto–Oncogene and Genetic Sequences Encoding a Receptor–like Protein", *EMBO J.*, 5(9):2197–2202 (1986) [Roebroek I].

A. Roebroek et al, "Characterization of Human c–fes/fps Reveals a New Transcription Unit (fur) in the Immediately Upstream Region of the Proto–Oncogene", *Molec. Biol. Rep.*, 11:117–125 (1986) [Roebroek II].

A. Roeroek et al, "cDNA Sequence of a *Drosophila melanogaster* Gene, Dfur1, Encoding a Protein Structurally Related to the Subtilisin–like Proprotein Processing Enzyme Furin", *FEBS Letters*, 289(2):133–137 (Sep., 1991) [Roebroek III].

R. Wise et al, "Expression of a Human Prorotein Processing Enzyme: Correct Cleavage of the von Willebrand Factor Precursor at a Paired Basic Amino Acid Site", *Proc. Natl. Acad. Sci. USA*, 87:9378–9382 (Dec., 1990) [Wise I].

R. Wise et al, "Expression of a Human Proprotein Processing Enzyme that Correctly Cleaves the von Willebrand Factor Precursor at its Dibasis Amino Acid Recognition Site", The International Society of Hematology 23rd Congress the American Society of Hematology 32nd Annual Meeting, (Abstract of talk at meeting, Aug. 20, 1990) [Wise II].

A. Rehemtulla et al, "Preferred Sequence Requirements for Cleavage of Pro–von Willebrand Factor by Propeptide–Processing Enzymes", *Blood*, 79(9):2349–2355 (May 1, 1992) [Rehemtulla I].

A. Rehemtulla et al, "Regulation of PACE Propeptide–Processing Activity: Requirement for a Post–Endoplasmic Reticulum Compartment and Autoproteolytic Activation", *Proc. Natl. Acad. Sci. USA*, 89:8235–8239 (Sep., 1992) [Rehemtulla II].

A. Rehemtulla et al, "Protein Processing within the Secretory Pathway", *Current Opinion in Biotechnology*, 3:560–565 (Oct., 1992) [Rehemtulla III].

A. Rehemtulla et al, "PACE4 is a Member of the Mammalian Propeptidase Family that has Overlapping but not Identical Substrate Specificity to Pace", *Biochemistry*, 32(43):11586–11590 (Nov. 2, 1993) [Rehemtulla IV].

W. van de Ven et al, "Furin: The Prototype Mammalian Subtilisin–like Proprotein–Processing Enzyme", *Enzyme*, 45:257–270 (Jun., 1991) [van de Ven I].

W. van de Ven et al, "Furin is a Subtilisin–like Proprotein Processing Enzyme in Higher Eukaryotes", *Mol. Biol. Rep.*, 14:265–275 (1990) [van de Ven II].

Y. Misumi et al, "Sequence of the cDNA Encoding Rat Furin, a Possible Propeptide–Processing Endoprotease", *Nucleic Acid Res.*, 18(22):6719 (Nov. 25, 1990) [Misumi I].

Y. Misumi et al, "Functional Expression of Furin Demonstrating its Intracellular Localization and Endoprotease Activity for Processing of Proalbumin and Complement Pro–C3", *J. Biol. Chem.*, 266(25):16954–16959 (Sep. 5, 1991) [Misumi II].

K. Hatsuzawa et al, "Structure and Expression of Mouse Furin, a Yeast Kex2–related Protease", *J. Biol. Chem.*, 265(36):22075–22078 (Dec. 25, 1990) [Hatsuzawa I].

K. Hatsuzawa et al, "Purification and Characterization of Furin, a Kex2–like Processing Endoprotease, Produced in Chinese Hamster Ovary Cells", *J. Biol. Chem.*, 267(23):16094–16099 (Aug. 15, 1992) [Hatsuzawa II].

D. Foster et al, "Endoproteolytic Processing of the Recombinant Protein C Precursor to Mature 2–Chain Protein C or Activated Protein C in Baby Hamster Kidney Cells", *Thrombosis and Haemostasis*, 62:321 (1989).

C. Derian et al, "Inhibitors of 2–Ketoglutarate–dependent Dioxygenases Block Aspartly beta–Hydroxylation of Recombinant Human Factor IX in Several Mammalian Expression Systems", *J. Biol. Chem.*, 264(12):6615–6618 (Apr. 25, 1989).

S. Smeekens et al, "Identification of a Human Insulinoma cDNA Encoding a Novel Mammalian Protein Structurally Related to the Yeast Dibasic Processing Protease Kex2", *J. Biol. Chem.*, 265(6):2997–3000 (Feb. 25, 1990).

B. Furie et al, "The Molecular Basis of Blood Coagulation", *Cell*, 53:505–518 (May 20, 1988).

G. Thomas et al, "Yeast KEX2 Endopeptidase Correctly Cleaves a Neuroendocrine Prohormone in Mammalian Cells", *Science*, 241:226–230 (Jul. 8, 1988).

I. Dickerson et al, "Biosynthesis and Posttranslational Processing of Site–directed Endoproteolytic Cleavage Mutants of Pro–neuropeptide Y in Mouse Pituitary Cells", *J. Biol. Chem.*, 265(5):2462–2469 (Feb. 15, 1990).

T. Achstetter et al, "Hormone Processing and Membrane–bound Proteinases in Yeast", *EMBO J.*, 4(1):173–177 (1985).

K. Mizuno et al, "A Membrane–Bound, Calcium–Dependent Protease in Yeast alpha–Cell Cleaving on the Carboxyl Side of Paired Basic Residues", *Biochem. Biophys. Res. Commun.*, 144(2):807–814 (Apr. 29, 1987).

E. Wang et al, "Recombinant Human Bone Morphogenetic Protein Induces Bone Formation", *Proc. Natl. Acad. Sci. USA*, 87:2220–2224 (Mar.,1990).

I. Bathurst et al, "Yeast KEX2 Protease has the Properties of a Human Proalbumin Converting Enzyme", *Science*, 235:348–350 (Jan. 16, 1987).

N. Seidah et al, "cDNA Sequence of Two Distinct Pituitary Proteins Homologous to KEX2 and Furin Gene Products: Tissue–Specific mRNAs Encoding Candidates for Pro–Hormone Processing Proteinases", *DNA and Cell Biology*, 9(6):415–424 (1990).

M. Pantoliano et al, "Protein Engineering of Subtilisin BPN': Enhanced Stabilization Through the Introduction of Two Cysteins to Form a Disulfide Bond", *Biochem*, 26:2077–2082 (Apr. 21, 1987).

A. Russell et al, "Electrostatic Effects on Modification of Charged Groups in the Active Site Cleft of Subtilisin by Protein Engineering", *J. Mol. Biol.*, 193:803–813 (Feb. 20, 1987).

J. Wells et al, "Designing Substrate Specificity by Protein Engineering of Electrostatic Interactions", *Proc. Natl. Acad. Sci. USA*, 84:1219–1223 (Mar., 1987).

Y. Ikehara et al, "Functional Expression of Furin Demonstrating its Intracellular Localization and Proprotein–Processing Activity", Abstract No. 3SC–1630, *Cell Struct. Function*, 16:541 (1991).

P. Bresnahan et al, "Human fur Gene Encodes a Yeast KEX2–like Endoprotease that Cleaves Pro–beta–NGF in Vivo", *J. Cell. Biol.*, 111(No. 6, Pt. 2):2851–2859 (Dec., 1990).

E. Fortkamp et al, "Cloning and Expression in *Escherichia coli* of a Synthetic DNA for Hirudin, the Blood Coagulation Inhibitor in the Leech", *DNA*, 5(6):511–517 (1986).

J. Schalken et al, "fur Gene Expression as a Discriminating Marker for Small Cell and Nonsmall Cell Lung Carcinomas", *J. Clin. Invest.*, 80:1545–1549 (Dec., 1987).

M. Kiefer et al, "Identification of a Second Human Subtilisin–like Protease Gene in the fes/fps Region of Chromosome 15", *DNA and Cell Biol.*, 10(10):757–769 (1991).

L. Wasley et al, "PACE/Furin can Process the Vitamin K–dependent Pro–factor IX Precursor within the Secretory Pathway", *J. Biol. Chem.*, 268(12):8458–8465 (Apr. 25, 1993).

H. Ehrlich et al, "Direct Expression of Recombinant Activated Human Protein C, a Serine Protease", *J. Biol. Chem.*, 264(24):14298–14304 (Aug. 25, 1989).

Fig. 1A

| | | | | | | | | | | | | |
|---|---|---|---|---|---|---|---|---|---|---|---|---|
| ATG | GAG | CTG | AGG | CCC | TGG | TTG | CTA | TGG | GTG | GTA | GCA | GCA | 39 |
| Met | Glu | Leu | Arg | Pro | Trp | Leu | Leu | Trp | Val | Val | Ala | Ala | |
| 1 | | | | 5 | | | | | 10 | | | | |

| ACA | GGA | ACC | TTG | GTC | CTG | CTA | GCA | GCT | GAT | GCT | CAG | GGC | 78 |
|---|---|---|---|---|---|---|---|---|---|---|---|---|---|
| Thr | Gly | Thr | Leu | Val | Leu | Leu | Ala | Ala | Asp | Ala | Gln | Gly | |
| | 15 | | | | 20 | | | | | 25 | | | |

| CAG | AAG | GTC | TTC | ACC | AAC | ACG | TGG | GCT | GTG | CGC | ATC | CCT | 117 |
|---|---|---|---|---|---|---|---|---|---|---|---|---|---|
| Gln | Lys | Val | Phe | Thr | Asn | Thr | Trp | Ala | Val | Arg | Ile | Pro | |
| | | | 30 | | | | | 35 | | | | | |

| GGA | GGC | CCA | GCG | GTG | GCC | AAC | AGT | GTG | GCA | CGG | AAG | CAT | 156 |
|---|---|---|---|---|---|---|---|---|---|---|---|---|---|
| Gly | Gly | Pro | Ala | Val | Ala | Asn | Ser | Val | Ala | Arg | Lys | His | |
| 40 | | | | | 45 | | | | | 50 | | | |

| GGG | TTC | CTC | AAC | CTG | GGC | CAG | ATC | TTC | GGG | GAC | TAT | TAC | 195 |
|---|---|---|---|---|---|---|---|---|---|---|---|---|---|
| Gly | Phe | Leu | Asn | Leu | Gly | Gln | Ile | Phe | Gly | Asp | Tyr | Tyr | |
| | | 55 | | | | | 60 | | | | | 65 | |

| CAC | TTC | TGG | CAT | CGA | GGA | GTG | ACG | AAG | CGG | TCC | CTG | TCG | 234 |
|---|---|---|---|---|---|---|---|---|---|---|---|---|---|
| His | Phe | Trp | His | Arg | Gly | Val | Thr | Lys | Arg | Ser | Leu | Ser | |
| | | | | 70 | | | | | 75 | | | | |

| CCT | CAC | CGC | CCG | CGG | CAC | AGC | CGG | CTG | CAG | AGG | GAG | CCT | 273 |
|---|---|---|---|---|---|---|---|---|---|---|---|---|---|
| Pro | His | Arg | Pro | Arg | His | Ser | Arg | Leu | Gln | Arg | Glu | Pro | |
| | 80 | | | | | 85 | | | | | 90 | | |

| CAA | GTA | CAG | TGG | CTG | GAA | CAG | CAG | GTG | GCA | AAG | CGA | CGG | 312 |
|---|---|---|---|---|---|---|---|---|---|---|---|---|---|
| Gln | Val | Gln | Trp | Leu | Glu | Gln | Gln | Val | Ala | Lys | Arg | Arg | |
| | | | 95 | | | | | | 100 | | | | |

| ACT | AAA | CGG | GAC | GTG | TAC | CAG | GAG | CCC | ACA | GAC | CCC | AAG | 351 |
|---|---|---|---|---|---|---|---|---|---|---|---|---|---|
| Thr | Lys | Arg | Asp | Val | Tyr | Gln | Glu | Pro | Thr | Asp | Pro | Lys | |
| 105 | | | | | 110 | | | | | 115 | | | |

| TTT | CCT | CAG | CAG | TGG | TAC | CTG | TCT | GGT | GTC | ACT | CAG | CGG | 390 |
|---|---|---|---|---|---|---|---|---|---|---|---|---|---|
| Phe | Pro | Gln | Gln | Trp | Tyr | Leu | Ser | Gly | Val | Thr | Gln | Arg | |
| | | | 120 | | | | | 125 | | | | 130 | |

| GAC | CTG | AAT | GTG | AAG | GCG | GCC | TGG | GCG | CAG | GGC | TAC | ACA | 429 |
|---|---|---|---|---|---|---|---|---|---|---|---|---|---|
| Asp | Leu | Asn | Val | Lys | Ala | Ala | Trp | Ala | Gln | Gly | Tyr | Thr | |
| | | | | 135 | | | | | 140 | | | | |

| GGG | CAC | GGC | ATT | GTG | GTC | TCC | ATT | CTG | GAC | GAT | GGC | ATC | 468 |
|---|---|---|---|---|---|---|---|---|---|---|---|---|---|
| Gly | His | Gly | Ile | Val | Val | Ser | Ile | Leu | Asp | Asp | Gly | Ile | |
| | 145 | | | | | 150 | | | | | 155 | | |

Fig. 1B

| | | | | | | | | | | | |
|---|---|---|---|---|---|---|---|---|---|---|---|
| GAG | AAG | AAC | CAC | CCG | GAC | TTG | GCA | GGC | AAT | TAT | GAT | CCT | 507 |
| Glu | Lys | Asn | His | Pro | Asp | Leu | Ala | Gly | Asn | Tyr | Asp | Pro | |
| | | | 160 | | | | | 165 | | | | | |

```
GAG AAG AAC CAC CCG GAC TTG GCA GGC AAT TAT GAT CCT      507
Glu Lys Asn His Pro Asp Leu Ala Gly Asn Tyr Asp Pro
            160                 165

GGG GCC AGT TTT GAT GTC AAT GAC CAG GAC CCT GAC CCC      546
Gly Ala Ser Phe Asp Val Asn Asp Gln Asp Pro Asp Pro
170             175                 180

CAG CCT CGG TAC ACA CAG ATG AAT GAC AAC AGG CAC GGC      585
Gln Pro Arg Tyr Thr Gln Met Asn Asp Asn Arg His Gly
        185                 190                 195

ACA CGG TGT GCG GGG GAA GTG GCT GCG GTG GCC AAC AAC      624
Thr Arg Cys Ala Gly Glu Val Ala Ala Val Ala Asn Asn
                200                 205

GGT GTC TGT GGT GTA GGT GTG GCC TAC AAC GCC CGC ATT      663
Gly Val Cys Gly Val Gly Val Ala Tyr Asn Ala Arg Ile
            210                 215                 220

GGA GGG GTG CGC ATG CTG GAT GGC GAG GTG ACA GAT GCA      702
Gly Gly Val Arg Met Leu Asp Gly Glu Val Thr Asp Ala
                225                 230

GTG GAG GCA CGC TCG CTG GGC CTG AAC CCC AAC CAC ATC      741
Val Glu Ala Arg Ser Leu Gly Leu Asn Pro Asn His Ile
235                 240                 245

CAC ATC TAC AGT GCC AGC TGG GGC CCC GAG GAT GAC GGC      780
His Ile Tyr Ser Ala Ser Trp Gly Pro Glu Asp Asp Gly
            250                 255                 260

AAG ACA GTG GAT GGG CCA GCC CGC CTC GCC GAG GAG GCC      819
Lys Thr Val Asp Gly Pro Ala Arg Leu Ala Glu Glu Ala
                265                 270

TTC TTC CGT GGG GTT AGC CAG GGC CGA GGG GGG CTG GGC      858
Phe Phe Arg Gly Val Ser Gln Gly Arg Gly Gly Leu Gly
        275                 280                 285

TCC ATC TTT GTC TGG GCC TCG GGG AAC GGG GGC CGG GAA      897
Ser Ile Phe Val Trp Ala Ser Gly Asn Gly Gly Arg Glu
            290                 295

CAT GAC AGC TGC AAC TGC GAC GGC TAC ACC AAC AGT ATC      936
His Asp Ser Cys Asn Cys Asp Gly Tyr Thr Asn Ser Ile
300                 305                 310
```

Fig. 1C

```
TAC ACG CTG TCC ATC AGC AGC GCC ACG CAG TTT GGC AAC        975
Tyr Thr Leu Ser Ile Ser Ser Ala Thr Gln Phe Gly Asn
        315             320                 325

GTG CCG TGG TAC AGC GAG GCC TGC TCG TCC ACA CTG GCC       1014
Val Pro Trp Tyr Ser Glu Ala Cys Ser Ser Thr Leu Ala
                330                 335

ACG ACC TAC AGC AGT GGC AAC CAG AAT GAG AAG CAG ATC       1053
Thr Thr Tyr Ser Ser Gly Asn Gln Asn Glu Lys Gln Ile
    340                 345                 350

GTG ACG ACT GAC TTG CGG CAG AAG TGC ACG GAG TCT CAC       1092
Val Thr Thr Asp Leu Arg Gln Lys Cys Thr Glu Ser His
            355                 360

ACG GGC ACC TCA GCC TCT GCC CCC TTA GCA GCC GGC ATC       1131
Thr Gly Thr Ser Ala Ser Ala Pro Leu Ala Ala Gly Ile
365             370                 375

ATT GCT CTC ACC CTG GAG GCC AAT AAG AAC CTC ACA TGG       1170
Ile Ala Leu Thr Leu Glu Ala Asn Lys Asn Leu Thr Trp
        380                 385                 390

CGG GAC ATG CAA CAC CTG GTG GTA CAG ACC TCG AAG CCA       1209
Arg Asp Met Gln His Leu Val Val Gln Thr Ser Lys Pro
                395                 400

GCC CAC CTC AAT GCC AAC GAC TGG GCC ACC AAT GGT GTG       1248
Ala His Leu Asn Ala Asn Asp Trp Ala Thr Asn Gly Val
    405                 410                 415

GGG CGG AAA GTG AGC CAC TCA TAT GGC TAC GGG CTT TTG       1287
Gly Arg Lys Val Ser His Ser Tyr Gly Tyr Gly Leu Leu
            420                 425

GAC GCA GGC GCC ATG GTG GCC CTG GCC CAG AAT TGG ACC       1326
Asp Ala Gly Ala Met Val Ala Leu Ala Gln Asn Trp Thr
430             435                 440

ACA GTG GCC CCC CAG CGG AAG TGC ATC ATC GAC ATC CTC       1365
Thr Val Ala Pro Gln Arg Lys Cys Ile Ile Asp Ile Leu
        445                 450                 455

ACC GAG CCC AAA GAC ATC GGG AAA CGG CTC GAG GTG CGG       1404
Thr Glu Pro Lys Asp Ile Gly Lys Arg Leu Glu Val Arg
                460                 465
```

Fig. 1D

```
AAG ACC GTG ACC GCG TGC CTG GGC GAG CCC AAC CAC ATC    1443
Lys Thr Val Thr Ala Cys Leu Gly Glu Pro Asn His Ile
    470             475                 480

ACT CGG CTG GAG CAC GCT CAG GCG CGG CTC ACC CTG TCC    1482
Thr Arg Leu Glu His Ala Gln Ala Arg Leu Thr Leu Ser
                485                 490

TAT AAT CGC CGT GGC GAC CTG GCC ATC CAC CTG GTC AGC    1521
Tyr Asn Arg Arg Gly Asp Leu Ala Ile His Leu Val Ser
495                 500                 505

CCC ATG GGC ACC CGC TCC ACC CTG CTG GCA GCC AGG CCA    1560
Pro Met Gly Thr Arg Ser Thr Leu Leu Ala Ala Arg Pro
        510                 515                 520

CAT GAC TAC TCC GCA GAT GGG TTT AAT GAC TGG GCC TTC    1599
His Asp Tyr Ser Ala Asp Gly Phe Asn Asp Trp Ala Phe
                525                 530

ATG ACA ACT CAT TCC TGG GAT GAG GAT CCC TCT GGC GAG    1638
Met Thr Thr His Ser Trp Asp Glu Asp Pro Ser Gly Glu
        535                 540                 545

TGG GTC CTA GAG ATT GAA AAC ACC AGC GAA GCC AAC AAC    1677
Trp Val Leu Glu Ile Glu Asn Thr Ser Glu Ala Asn Asn
                550                 555

TAT GGG ACG CTG ACC AAG TTC ACC CTC GTA CTC TAT GGC    1716
Tyr Gly Thr Leu Thr Lys Phe Thr Leu Val Leu Tyr Gly
560                 565                 570

ACC GCC CCT GAG GGG CTG CCC GTA CCT CCA GAA AGC AGT    1755
Thr Ala Pro Glu Gly Leu Pro Val Pro Pro Glu Ser Ser
        575                 580                 585

GGC TGC AAG ACC CTC ACG TCC AGT CAG GCC TGT GTG GTG    1794
Gly Cys Lys Thr Leu Thr Ser Ser Gln Ala Cys Val Val
                590                 595

TGC GAG GAA GGC TTC TCC CTG CAC CAG AAG AGC TGT GTC    1833
Cys Glu Glu Gly Phe Ser Leu His Gln Lys Ser Cys Val
    600                 605                 610

CAG CAC TGC CCT CCA GGC TTC GCC CCC CAA GTC CTC GAT    1872
Gln His Cys Pro Pro Gly Phe Ala Pro Gln Val Leu Asp
                615                 620
```

Fig. 1E

```
ACG CAC TAT AGC ACC GAG AAT GAC GTG GAG ACC ATC CGG    1911
Thr His Tyr Ser Thr Glu Asn Asp Val Glu Thr Ile Arg
625             630                 635

GCC AGC GTC TGC GCC CCC TGC CAC GCC TCA TGT GCC ACA    1950
Ala Ser Val Cys Ala Pro Cys His Ala Ser Cys Ala Thr
        640             645                 650

TGC CAG GGG CCG GCC CTG ACA GAC TGC CTC AGC TGC CCC    1989
Cys Gln Gly Pro Ala Leu Thr Asp Cys Leu Ser Cys Pro
                655                 660

AGC CAC GCC TCC TTG GAC CCT GTG GAG CAG ACT TGC TCC    2028
Ser His Ala Ser Leu Asp Pro Val Glu Gln Thr Cys Ser
    665             670                 675

CGG CAA AGC CAG AGC AGC CGA GAG TCC CCG CCA CAG CAG    2067
Arg Gln Ser Gln Ser Ser Arg Glu Ser Pro Pro Gln Gln
                680             685

CAG CCA CCT CGG CTG CCC CCG GAG GTG GAG GCG GGG CAA    2106
Gln Pro Pro Arg Leu Pro Pro Glu Val Glu Ala Gly Gln
690                 695                 700

CGG CTG CGG GCA GGG CTG CTG CCC TCA CAC CTG CCT GAG    2145
Arg Leu Arg Ala Gly Leu Leu Pro Ser His Leu Pro Glu
        705             710                 715

GTG GTG GCC GGC CTC AGC TGC GCC TTC ATC GTG CTG GTC    2184
Val Val Ala Gly Leu Ser Cys Ala Phe Ile Val Leu Val
                720                 725

TTC GTC ACT GTC TTC CTG GTC CTG CAG CTG CGC TCT GGC    2223
Phe Val Thr Val Phe Leu Val Leu Gln Leu Arg Ser Gly
    730             735                 740

TTT AGT TTT CGG GGG GTG AAG GTG TAC ACC ATG GAC CGT    2262
Phe Ser Phe Arg Gly Val Lys Val Tyr Thr Met Asp Arg
                745             750

GGC CTC ATC TCC TAC AAG GGG CTG CCC CCT GAA GCC TGG    2301
Gly Leu Ile Ser Tyr Lys Gly Leu Pro Pro Glu Ala Trp
755             760                 765

CAG GAG GAG TGC CCG TCT GAC TCA GAA GAG GAC GAG GGC    2340
Gln Glu Glu Cys Pro Ser Asp Ser Glu Glu Asp Glu Gly
        770             775                 780
```

Fig. 1F

```
CGG GGC GAG AGG ACC GCC TTT ATC AAA GAC CAG AGC GCC   2379
Arg Gly Glu Arg Thr Ala Phe Ile Lys Asp Gln Ser Ala
                785             790

CTC TGA                                                2385
Leu End
    795
```

Fig. 2A

```
                                                        GAATTCG  -401
GAGATCTACA GGGCTGCCCC CGCCCGCGCC GGAGCTGGAG CCCAGGCCGA  -351
GCCCTGCCCT GGTCGCCGGC CGGGCCGAGG CCGCGCCGCC GCGCCTCCCC  -301
GCCTCCGCGC CGTGACGCTG CCGCCGGGCG CGGGGACCGC GCCGAGCCCA  -251
GGCCCCCGCC GCCGGGCTCT CCGCTCGGCC GAGGGGCGCC CGAGCCGCCG  -201
CGGCGGTCGC CTGGAAAAGT TTCCCCGCCA GGGCTCCCCA GGGGTCGGCA  -151
CTCTTCACCC TCCCGAGCCC TGCCCGTCTC GGCCCCATGC CCCCACCAGT  -101
CAGCCCCGGG CCACAGGCAG TGAGCAGGCA CCTGGGAGCC GAGGCCTGTG  - 51
ACCAGGCCAA GGAGACGGGC GCTCCAGGGT CCCAGCCACC TGTCCCCCCC  -  1
```

| | | | | | | | | | | |
|---|---|---|---|---|---|---|---|---|---|---|
| ATG | GAG | CTG | AGG | CCC | TGG | TTG | CTA | TGG | GTG | GTA | GCA | GCA | 39 |
| Met | Glu | Leu | Arg | Pro | Trp | Leu | Leu | Trp | Val | Val | Ala | Ala | |
| 1 | | | | 5 | | | | | 10 | | | | |

| ACA | GGA | ACC | TTG | GTC | CTG | CTA | GCA | GCT | GAT | GCT | CAG | GGC | 78 |
| Thr | Gly | Thr | Leu | Val | Leu | Leu | Ala | Ala | Asp | Ala | Gln | Gly | |
| | 15 | | | | 20 | | | | | 25 | | | |

| CAG | AAG | GTC | TTC | ACC | AAC | ACG | TGG | GCT | GTG | CGC | ATC | CCT | 117 |
| Gln | Lys | Val | Phe | Thr | Asn | Thr | Trp | Ala | Val | Arg | Ile | Pro | |
| | | | 30 | | | | | 35 | | | | | |

| GGA | GGC | CCA | GCG | GTG | GCC | AAC | AGT | GTG | GCA | CGG | AAG | CAT | 156 |
| Gly | Gly | Pro | Ala | Val | Ala | Asn | Ser | Val | Ala | Arg | Lys | His | |
| 40 | | | | | 45 | | | | | 50 | | | |

| GGG | TTC | CTC | AAC | CTG | GGC | CAG | ATC | TTC | GGG | GAC | TAT | TAC | 195 |
| Gly | Phe | Leu | Asn | Leu | Gly | Gln | Ile | Phe | Gly | Asp | Tyr | Tyr | |
| | | | 55 | | | | | 60 | | | | | 65 |

| CAC | TTC | TGG | CAT | CGA | GGA | GTG | ACG | AAG | CGG | TCC | CTG | TCG | 234 |
| His | Phe | Trp | His | Arg | Gly | Val | Thr | Lys | Arg | Ser | Leu | Ser | |
| | | | | 70 | | | | | 75 | | | | |

| CCT | CAC | CGC | CCG | CGG | CAC | AGC | CGG | CTG | CAG | AGG | GAG | CCT | 273 |
| Pro | His | Arg | Pro | Arg | His | Ser | Arg | Leu | Gln | Arg | Glu | Pro | |
| | | 80 | | | | | 85 | | | | | 90 | |

| CAA | GTA | CAG | TGG | CTG | GAA | CAG | CAG | GTG | GCA | AAG | CGA | CGG | 312 |
| Gln | Val | Gln | Trp | Leu | Glu | Gln | Gln | Val | Ala | Lys | Arg | Arg | |
| | | | | 95 | | | | | 100 | | | | |

| ACT | AAA | CGG | GAC | GTG | TAC | CAG | GAG | CCC | ACA | GAC | CCC | AAG | 351 |
| Thr | Lys | Arg | Asp | Val | Tyr | Gln | Glu | Pro | Thr | Asp | Pro | Lys | |
| 105 | | | | | 110 | | | | | 115 | | | |

| TTT | CCT | CAG | CAG | TGG | TAC | CTG | TCT | GGT | GTC | ACT | CAG | CGG | 390 |
| Phe | Pro | Gln | Gln | Trp | Tyr | Leu | Ser | Gly | Val | Thr | Gln | Arg | |
| | | 120 | | | | | 125 | | | | | 130 | |

Fig. 2B

```
GAC CTG AAT GTG AAG GCG GCC TGG GCG CAG GGC TAC ACA        429
Asp Leu Asn Val Lys Ala Ala Trp Ala Gln Gly Tyr Thr
            135             140

GGG CAC GGC ATT GTG GTC TCC ATT CTG GAC GAT GGC ATC        468
Gly His Gly Ile Val Val Ser Ile Leu Asp Asp Gly Ile
    145             150             155

GAG AAG AAC CAC CCG GAC TTG GCA GGC AAT TAT GAT CCT        507
Glu Lys Asn His Pro Asp Leu Ala Gly Asn Tyr Asp Pro
                160             165

GGG GCC AGT TTT GAT GTC AAT GAC CAG GAC CCT GAC CCC        546
Gly Ala Ser Phe Asp Val Asn Asp Gln Asp Pro Asp Pro
170             175             180

CAG CCT CGG TAC ACA CAG ATG AAT GAC AAC AGG CAC GGC        585
Gln Pro Arg Tyr Thr Gln Met Asn Asp Asn Arg His Gly
            185             190             195

ACA CGG TGT GCG GGG GAA GTG GCT GCG GTG GCC AAC AAC        624
Thr Arg Cys Ala Gly Glu Val Ala Ala Val Ala Asn Asn
                200             205

GGT GTC TGT GGT GTA GGT GTG GCC TAC AAC GCC CGC ATT        663
Gly Val Cys Gly Val Gly Val Ala Tyr Asn Ala Arg Ile
        210             215             220

GGA GGG GTG CGC ATG CTG GAT GGC GAG GTG ACA GAT GCA        702
Gly Gly Val Arg Met Leu Asp Gly Glu Val Thr Asp Ala
            225             230

GTG GAG GCA CGC TCG CTG GGC CTG AAC CCC AAC CAC ATC        741
Val Glu Ala Arg Ser Leu Gly Leu Asn Pro Asn His Ile
235             240             245

CAC ATC TAC AGT GCC AGC TGG GGC CCC GAG GAT GAC GGC        780
His Ile Tyr Ser Ala Ser Trp Gly Pro Glu Asp Asp Gly
            250             255             260

AAG ACA GTG GAT GGG CCA GCC CGC CTC GCC GAG GAG GCC        819
Lys Thr Val Asp Gly Pro Ala Arg Leu Ala Glu Glu Ala
                265             270

TTC TTC CGT GGG GTT AGC CAG GGC CGA GGG GGG CTG GGC        858
Phe Phe Arg Gly Val Ser Gln Gly Arg Gly Gly Leu Gly
        275             280             285

TCC ATC TTT GTC TGG GCC TCG GGG AAC GGG GGC CGG GAA        897
Ser Ile Phe Val Trp Ala Ser Gly Asn Gly Gly Arg Glu
            290             295
```

Fig. 2C

| | | | | | | | | | | | | |
|---|---|---|---|---|---|---|---|---|---|---|---|---|
| CAT | GAC | AGC | TGC | AAC | TGC | GAC | GGC | TAC | ACC | AAC | AGT | ATC | 936 |
| His | Asp | Ser | Cys | Asn | Cys | Asp | Gly | Tyr | Thr | Asn | Ser | Ile | |
| 300 | | | | 305 | | | | | 310 | | | | |

```
CAT GAC AGC TGC AAC TGC GAC GGC TAC ACC AAC AGT ATC    936
His Asp Ser Cys Asn Cys Asp Gly Tyr Thr Asn Ser Ile
300             305                 310

TAC ACG CTG TCC ATC AGC AGC GCC ACG CAG TTT GGC AAC    975
Tyr Thr Leu Ser Ile Ser Ser Ala Thr Gln Phe Gly Asn
        315             320                 325

GTG CCG TGG TAC AGC GAG GCC TGC TCG TCC ACA CTG GCC   1014
Val Pro Trp Tyr Ser Glu Ala Cys Ser Ser Thr Leu Ala
                330             335

ACG ACC TAC AGC AGT GGC AAC CAG AAT GAG AAG CAG ATC   1053
Thr Thr Tyr Ser Ser Gly Asn Gln Asn Glu Lys Gln Ile
        340             345                 350

GTG ACG ACT GAC TTG CGG CAG AAG TGC ACG GAG TCT CAC   1092
Val Thr Thr Asp Leu Arg Gln Lys Cys Thr Glu Ser His
            355                 360

ACG GGC ACC TCA GCC TCT GCC CCC TTA GCA GCC GGC ATC   1131
Thr Gly Thr Ser Ala Ser Ala Pro Leu Ala Ala Gly Ile
365                 370                 375

ATT GCT CTC ACC CTG GAG GCC AAT AAG AAC CTC ACA TGG   1170
Ile Ala Leu Thr Leu Glu Ala Asn Lys Asn Leu Thr Trp
        380                 385                 390

CGG GAC ATG CAA CAC CTG GTG GTA CAG ACC TCG AAG CCA   1209
Arg Asp Met Gln His Leu Val Val Gln Thr Ser Lys Pro
                395                 400

GCC CAC CTC AAT GCC AAC GAC TGG GCC ACC AAT GGT GTG   1248
Ala His Leu Asn Ala Asn Asp Trp Ala Thr Asn Gly Val
        405                 410                 415

GGC CGG AAA GTG AGC CAC TCA TAT GGC TAC GGG CTT TTG   1287
Gly Arg Lys Val Ser His Ser Tyr Gly Tyr Gly Leu Leu
            420                 425

GAC GCA GGC GCC ATG GTG GCC CTG GCC CAG AAT TGG ACC   1326
Asp Ala Gly Ala Met Val Ala Leu Ala Gln Asn Trp Thr
430                 435                 440

ACA GTG GCC CCC CAG CGG AAG TGC ATC ATC GAC ATC CTC   1365
Thr Val Ala Pro Gln Arg Lys Cys Ile Ile Asp Ile Leu
        445                 450                 455

ACC GAG CCC AAA GAC ATC GGG AAA CGG CTC GAG GTG CGG   1404
Thr Glu Pro Lys Asp Ile Gly Lys Arg Leu Glu Val Arg
                460                 465
```

Fig. 2D

| | |
|---|---|
| AAG ACC GTG ACC GCG TGC CTG GGC GAG CCC AAC CAC ATC<br>Lys Thr Val Thr Ala Cys Leu Gly Glu Pro Asn His Ile<br>    470                                    475                      480 | 1443 |
| ACT CGG CTG GAG CAC GCT CAG GCG CGG CTC ACC CTG TCC<br>Thr Arg Leu Glu His Ala Gln Ala Arg Leu Thr Leu Ser<br>                      485                              490 | 1482 |
| TAT AAT CGC CGT GGC GAC CTG GCC ATC CAC CTG GTC AGC<br>Tyr Asn Arg Arg Gly Asp Leu Ala Ile His Leu Val Ser<br>495                          500                          505 | 1521 |
| CCC ATG GGC ACC CGC TCC ACC CTG CTG GCA GCC AGG CCA<br>Pro Met Gly Thr Arg Ser Thr Leu Leu Ala Ala Arg Pro<br>          510                          515                    520 | 1560 |
| CAT GAC TAC TCC GCA GAT GGG TTT AAT GAC TGG GCC TTC<br>His Asp Tyr Ser Ala Asp Gly Phe Asn Asp Trp Ala Phe<br>                      525                            530 | 1599 |
| ATG ACA ACT CAT TCC TGG GAT GAG GAT CCC TCT GGC GAG<br>Met Thr Thr His Ser Trp Asp Glu Asp Pro Ser Gly Glu<br>    535                            540                      545 | 1638 |
| TGG GTC CTA GAG ATT GAA AAC ACC AGC GAA GCC AAC AAC<br>Trp Val Leu Glu Ile Glu Asn Thr Ser Glu Ala Asn Asn<br>                550                          555 | 1677 |
| TAT GGG ACG CTG ACC AAG TTC ACC CTC GTA CTC TAT GGC<br>Tyr Gly Thr Leu Thr Lys Phe Thr Leu Val Leu Tyr Gly<br>560                          565                          570 | 1716 |
| ACC GCC CCT GAG GGG CTG CCC GTA CCT CCA GAA AGC AGT<br>Thr Ala Pro Glu Gly Leu Pro Val Pro Pro Glu Ser Ser<br>          575                          580                    585 | 1755 |
| GGC TGC AAG ACC CTC ACG TCC AGT CAG GCC TGT GTG GTG<br>Gly Cys Lys Thr Leu Thr Ser Ser Gln Ala Cys Val Val<br>                      590                            595 | 1794 |
| TGC GAG GAA GGC TTC TCC CTG CAC CAG AAG AGC TGT GTC<br>Cys Glu Glu Gly Phe Ser Leu His Gln Lys Ser Cys Val<br>    600                            605                      610 | 1833 |
| CAG CAC TGC CCT CCA GGC TTC GCC CCC CAA GTC CTC GAT<br>Gln His Cys Pro Pro Gly Phe Ala Pro Gln Val Leu Asp<br>                      615                            620 | 1872 |
| ACG CAC TAT AGC ACC GAG AAT GAC GTG GAG ACC ATC CGG<br>Thr His Tyr Ser Thr Glu Asn Asp Val Glu Thr Ile Arg<br>625                          630                          635 | 1911 |

Fig. 2E

| | | | | | | | | | | | |
|---|---|---|---|---|---|---|---|---|---|---|---|
| GCC | AGC | GTC | TGC | GCC | CCC | TGC | CAC | GCC | TCA | TGT | GCC | ACA | 1950
| Ala | Ser | Val | Cys | Ala | Pro | Cys | His | Ala | Ser | Cys | Ala | Thr |
| | | 640 | | | | | 645 | | | | | 650 |

```
GCC AGC GTC TGC GCC CCC TGC CAC GCC TCA TGT GCC ACA      1950
Ala Ser Val Cys Ala Pro Cys His Ala Ser Cys Ala Thr
        640             645                 650

TGC CAG GGG CCG GCC CTG ACA GAC TGC CTC AGC TGC CCC      1989
Cys Gln Gly Pro Ala Leu Thr Asp Cys Leu Ser Cys Pro
                655             660

AGC CAC GCC TCC TTG GAC CCT GTG GAG CAG ACT TGC TCC      2028
Ser His Ala Ser Leu Asp Pro Val Glu Gln Thr Cys Ser
    665             670                 675

CGG CAA AGC CAG AGC AGC CGA GAG TCC CCG CCA CAG CAG      2067
Arg Gln Ser Gln Ser Ser Arg Glu Ser Pro Pro Gln Gln
            680             685

CAG CCA CCT CGG CTG CCC CCG GAG GTG GAG GCG GGG CAA      2106
Gln Pro Pro Arg Leu Pro Pro Glu Val Glu Ala Gly Gln
690             695                 700

CGG CTG CGG GCA GGG CTG CTG CCC TCA CAC CTG CCT GAG      2145
Arg Leu Arg Ala Gly Leu Leu Pro Ser His Leu Pro Glu
        705             710                 715

GTG GTG GCC GGC CTC AGC TGC GCC TTC ATC GTG CTG GTC      2184
Val Val Ala Gly Leu Ser Cys Ala Phe Ile Val Leu Val
                720             725

TTC GTC ACT GTC TTC CTG GTC CTG CAG CTG CGC TCT GGC      2223
Phe Val Thr Val Phe Leu Val Leu Gln Leu Arg Ser Gly
    730             735                 740

TTT AGT TTT CGG GGG GTG AAG GTG TAC ACC ATG GAC CGT      2262
Phe Ser Phe Arg Gly Val Lys Val Tyr Thr Met Asp Arg
            745             750

GGC CTC ATC TCC TAC AAG GGG CTG CCC CCT GAA GCC TGG      2301
Gly Leu Ile Ser Tyr Lys Gly Leu Pro Pro Glu Ala Trp
755             760                 765

CAG GAG GAG TGC CCG TCT GAC TCA GAA GAG GAC GAG GGC      2340
Gln Glu Glu Cys Pro Ser Asp Ser Glu Glu Asp Glu Gly
        770             775                 780

CGG GGC GAG AGG ACC GCC TTT ATC AAA GAC CAG AGC GCC      2379
Arg Gly Glu Arg Thr Ala Phe Ile Lys Asp Gln Ser Ala
                785             790

CTC TGA TGA GCCCACTGCC CACCCCCTCA AGCCAATCCC CTCCTTGGGC  2428
Leu
```

Fig. 2F

```
ACTTTTTAAT TCACCAAAGT ATTTTTTTAT CTTGGGACTG GGTTTGGACC  2478
CCAGCTGGGA GGCAAGAGGG GTGGAGACTG TTTCCCATCC TACCCTCGGG  2528
CCCACCTGGC CACCTGAGGT GGGCCCAGGA CCAGCTGGGG CGTGGGGAGG  2578
GCCGTACCCC ACCCTCAGCA CCCCTTCCAT GTGGAGAAAG GAGTGAAACC  2628
TTTAGGGCAG CTTGCCCCGG CCCCGGCCCC AGCCAGAGTT CCTGCGGAGT  2678
GAAGAGGGGC AGCCCTTGCT TGTTGGGATT CCTGACCCAG GCCGCAGCTC  2728
TTGCCCTTCC CTGTCCCTCT AAAGCAATAA TGGTCCCATC CAGGCAGTCG  2778
GGGGCTGGCC TAGGAGATAT CTGAGGGAGG AGGCCACCTC TCCAAGGGCT  2828
TCTGCACCCT CCACCCTGTC CCCCAGCTCT GGTGAGTCTT GGCGGCAGCA  2878
GCCATCATAG GAAGGGACCA AGGCAAGGCA GGTGCCTCCA GGTGTGCACG  2928
TGGCATGTGG CCTGTGGCCT GTGTCCCATG ACCCACCCCT GTGCTCCGTG  2978
CCTCCACCAC CACTGGCCAC CAGGCTGGCG CAGCCAAGGC CGAAGCTCTG  3028
GCTGAACCCT GTGCTGGTGT CCTGACCACC CTCCCCTCTC TTGCACCCGC  3078
CTCTCCCGTC AGGGCCCAAG TCCTGTTTT CTGAGCCCGG GCTGCCTGGG  3128
CTGTTGGCAC TCACAGACCT GGAGCCCTG GGTGGGTGGT GGGGAGGGGC  3178
GCTGGCCCAG CCGGCCTCTC TGGCCTCCCA CCCGATGCTG CTTTCCCCTG  3228
TGGGGATCTC AGGGGCTGTT TGAGGATATA TTTTCACTTT GTGATTATTT  3278
CACTTTAGAT GCTGATGATT TGTTTTTGTA TTTTTAATGG GGGTAGCAGC  3328
TGGACTACCC ACGTTCTCAC ACCCACCGTC CGCCCTGCTC CTCCCTGGCT  3378
GCCCTGGCCC TGAGGTGTGG GGGCTGCAGC ATGTTGCTGA GGAGTGAGGA  3428
ATAGTTGAGC CCCAAGTCCT GAAGAGGCGG GCCAGCCAGG CGGGCTCAAG  3478
GAAAGGGGGT CCCAGTGGGA GGGGCAGGCT GACATCTGTG TTTCAAGTGG  3528
GGCTCGCCAT GCCGGGGTT CATAGGTCAC TGGCTCTCCA AGTGCCAGAG  3578
GTGGGCAGGT GGTGGCACTG AGCCCCCCA ACACTGTGCC CTGGTGGAGA  3628
AAGCACTGAC CTGTCATGCC CCCCTCAAAC CTCCTCTTCT GACGTGCCTT  3678
TTGCACCCCT CCCATTAGGA CAATCAGTCC CCTCCCATCT GGGAGTCCCC  3728
TTTTCTTTTC TACCCTAGCC ATTCCTGGTA CCCAGCCATC TGCCCAGGGG  3778
TGCCCCTCC TCTCCCATCC CCCTGCCCTC GTGGCCAGCC CGGCTGGTTT  3828
TGTAAGATAC TGGGTTGGTG CACAGTGATT TTTTTCTTGT AATTTAAACA  3878
GGCCCAGCAT TGCTGGTTCT ATTTAATGGA CATGAGATAA TGTTAGAGGT  3928
TTTAAAGTGA TTAAACGTGC AGACTATGCA AACCAAAAAA AAAAAAAAAA  3978
ACCGTCGACA AAGCGGCCGC                                   3998
```

EXPRESSION OF PACE IN HOST CELLS AND METHODS OF USE THEREOF

REFERENCE TO PRIOR U.S. PATENT APPLICATIONS

This U.S. Patent Application is a divisional of U.S. patent application Ser. No. 07/885,972 filed on May 20, 1992, and which issued as U.S. Pat. No. 5,460,950, which is a Continuation-in-Part of U.S. patent application Ser. No. 07/621,092, filed Nov. 26, 1990, now abandoned; Ser. No. 07/620,859, filed Nov. 29, 1990, now abandoned; Ser. No. 07/621,443, filed Nov. 29, 1990 now abandoned; and Ser. No. 07/621,457, filed Nov. 30, 1990, now abandoned.

BACKGROUND OF THE INVENTION

This invention relates generally to the production of proteins in recombinant host cells. More particularly, it relates to materials and methods for the production of mature forms of proteins from heterologous precursor polypeptides using a paired basic amino acid converting enzyme (PACE), which is expressed in selected host cells.

Many eukaryotic proteins are naturally synthesized as larger precursor polypeptides, which require further specific proteolytic processing for full maturation prior to secretion. However, many of these eukaryotic proteins or precursors when synthesized in bacteria fold incorrectly or inefficiently and, consequently, exhibit low specific activities. Posttranslational proteolysis is frequently required for the synthesis of fully biologically active, mature proteins and peptides in all eukaryotes examined, including yeast [R. S. Fuller et al., Ann. Rev. Physiol., 50:345 (1988)], invertebrates [R. H. Scheller et al., Cell, 32:7 (1983)], and mammalian cells [J. Douglass et al., Ann. Rev. Biochem., 53:665 (1984); and W. S. Sossin et al., Neuron, 2, 1407 (1989)].

One of the early events in precursor protein maturation is endoproteolytic cleavage at the carboxyl side of paired basic amino acid sequences (e.g., -Lys-Arg- and -Arg-Arg-). This kind of endoproteolytic cleavage was initially inferred from the sequences of several endocrine and neuroendocrine precursor proteins and was first proposed from studies of proinsulin [D. F. Steiner et al., Science, 157:697 (1968); R. E. Chance et al., Science, 161:165 (1968)] and the ACTH/β-endorphin precursor, proopiomelanocortin (POMC) [M. Chretien and C. H. Li, Can. J. Biochem., 45:1163 (1967)]. Subsequent studies have revealed a broad spectrum of precursor proteins that require endoproteolysis at pairs of basic amino acids to yield mature peptides including serum factors [A. K. Bentley et al, Cell, 45:343 (1986)], viral proteins [C. M. Rice et al., Virology, 151:1 (1986); C. M. Rice et al., Science, 229:726 (1985); J. M. McCune et al., Cell, 53:55 (1988)], growth factors [L. E. Gentry et al., Mol. Cell Biol., 8:4162 (1988); K. Sharples et al., DNA, 6:239 (1987); M. Yanagisawa et al., Nature, 332:411 (1988); and Gray et al., Nature, 303:722 (1983)] and receptors [Y. Yosimasa, Science, 240:784 (1988)). See, also, Dickerson et al, J. Biol. Chem., 265:2462 (1990); Achsletter et al, EMBO J., 4:173 (1985); and Mizuno et al, Biochem. Biophys. Res. Commun., 144:807 (1987).

Cleavage at the site of a paired basic amino acid sequence removes many propeptides which function in a variety of roles in the processing of the mature protein. In certain cases the propeptide can mediate correct folding and disulfide bond formation within the protein sequence. In other cases the presence of the propeptide appears to be involved in γ-carboxylation of glutamic acid residues in vitamin K-dependent coagulation factors. γ-carboxylated proteins include Factor IX and Protein C, and certain bone-specific proteins, such as bone Gla protein/osteocalcin. The propeptide can also direct intracellular targeting and regulate the coordinate synthesis of multiple mature peptides from a single precursor polypeptide.

The sequences of the propeptide domains of certain vitamin K-dependent blood coagulation proteins have been published [See, Furie et al, Cell, 53:505 (1988)] and the size of the propeptide has been established for both Factor IX and Protein C. Factor IX is a zymogen of a serine protease that is an important component of the intrinsic pathway of the blood coagulation cascade. The protein is synthesized in the liver and undergoes extensive co- and post-translational modification prior to secretion. These modifications involve endoproteolytic processing to remove the pre- and propeptides, glycosylation, vitamin K-dependent γ-carboxylation of 12 amino-terminal glutamic acid residues and β-hydroxylation of a single aspartic acid residue.

The γ-carboxyglutamic acid residues confer metal binding properties on the mature Factor IX protein and may function similarly in the processing of the other vitamin K-dependent blood clotting proteins. These γ-carboxyglutamic acid residues are essential for coagulant activity. The gamma-carboxyglutamate (GLA) domain of Factor IX has also been identified as a major requirement for cell binding [Derian et al, J. Biol. Chem., 264(12):6615–6618 (1989)].

With the advance of genetic engineering, many eukaryotic proteins are being produced recombinantly in selected cell lines. For example, Chinese Hamster Ovary (CHO) DUKX cell lines producing recombinant Factor IX at high antigen levels (20 μg/ml/day) have been isolated. However, only 1–2% of that recombinant protein is γ-carboxylated, and therefore biologically active, in the presence of vitamin K3 [Kaufman et al, J. Biol. Chem., 261(21):9622–28 (1986)]. Additionally, amino-terminal sequencing of the recombinant protein has found that 50% of the recombinant Factor IX produced by the CHO cells retain the propeptide [Derian et al, J. Biol. Chem., 264(12): 6615–18 (1989)]. Presumably, the endoproteolytic processing enzyme of the CHO cells directing this cleavage was either saturated or simply inefficient in its function.

Several activities capable of cleaving at single or paired basic residues in vitro have been proposed as candidates for authentic mammalian precursor endoproteases. See, for example, Y. P. Loh and H. Gainer, in Brain Peptides, D. T. Krieger, M. J. Brownstein, J. B. Martin, Eds. (Wiley-Interscience, New York, 1983), pp.76–116; M. Chretien, et al. in Cell Biology of the Secretory Process (Karger, Basel, Switzerland, 1983), pp.214–246; A. J. Mason, et al., Nature, 303:300 (1983); P. J. Isackson et al., J. Cell. Biochem., 33:65 (1987); I. Lindberg et al., J. Neurochem., 42:1411 (1985); J. A. Cromlish et al., J. Biol. Chem., 261:10850 (1986); K. Docherty et al., J. Biol. Chem., 259:6041 (1984); T. C. Chang and Y. P. Loh, Endocrinology, 114, 2092 (1984); B. P. Noe et al., J. Cell. Biol., 99:578 (1984); U. P. Loh, J. Biol. Chem., 261:11949 (1986); H. W. Davidson et al., Biochem. J., 246:279 (1987); P. Gluschankof et al., J. Biol. Chem., 262:9615 (1987); C. Clamigrand et al., Biochem., 26:6018 (1987); S. O. Brennan and R. J. Peach, FEBS Letters, 229:167 (1988); R. S. Fuller et al., Proc. Natl. Acad. Sci. USA, 86:1434 (1989); K. Mizuno et al., Biochem. Biophys. Res. Comm., 159:305 (1989); I. C. Bathurst et al., Science, 235:348 (1987); and G. Thomas et al., Science, 241:226 (1988)].

Despite the fact that these candidate activities and other processing enzymes have been proposed as being involved in the propeptide processing reactions, these endoproteolytic candidates have either not been fully characterized or have not been shown to be a bona fide precursor cleaving endoprotease in vivo. The purification of proprotein cleavage enzymes has been hampered by their low levels of activity in mammalian tissue and by their membrane-associated nature. Purification of these specific proteases has been complicated additionally by non-specific cleavage of the assay substrates in vitro, and by contaminating proteases such as those released from lysosomes.

The yeast enzyme Kex2, encoded by the KEX2 gene, is a membrane-bound, $Ca^{++}$-dependent serine protease which functions late in the secretory pathway of *Saccharomyces cerevisiae*. The enzyme cleaves the polypeptide chains of prepro-killer toxin and prepro-α-factor of that microorganism at the paired basic amino acid sequences of Lys-Arg and Arg-Arg [D. Julius et al, *Cell*, 37:1075 (1984); D. Julius et al, *Cell*, 36:309 (1984); K. Mizuno et al., *Biochem. Biophys. Res. Commun.*, 156:246 (1988); R. S. Fuller et al., *Proc. Natl. Acad. Sci. USA*, 86:1434 (1989)]. Kex-2 has been considered to be a prototypic proprotein convertase.

Recently, co-expression of the yeast KEX2 gene with POMC in mammalian BSC-40 cells (a cell line which is incapable of processing this peptide precursor) reportedly resulted in the generation, by proteolytic cleavage at pairs of basic amino acids, of authentic neuroendocrine prohormone peptides, including γ-LPH and β-endorphin [Thomas et al, (1988), cited above]. Foster et al, *Thrombosis and Haemostasis*, 62:321 (1989) have reported that the yeast KEX2gene product cleaves the Protein C precursor to a two-chain form when the yeast endoprotease of the KEX2 gene and the wild-type Protein C precursor are coexpressed. However, propeptide processing and the effect of Kex2 expression have not been studied.

Two human DNA protease sequences, designated PC2 and fur, share some structural homology with each other and with the KEX2 gene sequence. PC2, a mammalian subtilisin-like protease, was identified by amplification of a human insulinoma cDNA library by the polymerase chain reaction using KEX2-derived primers. PC2, which has been implicated in the endoproteolytic processing of prohormones, shares a partial homology to the yeast Kex2 protease, especially in the putative active site domains [Smeekens et al, *J. Biol. Chem.*, 265:2997 (1990)]. To date, however, no functional activity has been demonstrated for the PC2 clone.

The availability of the complete Kex2 gene sequence also allowed the detection of significant homology between the Kex2 protein and "furin", the product of the partially characterized human fur gene. The fur locus was initially identified by its proximity (in the immediate upstream region) to the c-fes/fps proto-oncogene [A. J. M. Roebroek et al, *EMBO J.*, 5:2197 (1986)]. The complete nucleotide sequence of the putative coding region of the fur gene has been reported. Upon comparison, the human fur gene product has demonstrated structural homology with the subtilisin-type serine protease encoded by the KEX2 gene of the yeast *S. cerevisiae* [A. M. W. van den Ouweland et al, *Nucl. Acids Res.*, 18(3):664 (1990). This published cDNA coding sequence for fur is presented in FIG. 1 (SEQ ID NO: 1]. See, also, R. S. Fuller et al, *Science*, 246:482 (1989). However, no evidence of the expression of fur was reported.

An expression system has been developed which utilizes baculovirus vectors to introduce heterologous genes into insect cells in culture and subsequently effects the expression of the heterologous polypeptide. This has proven successful for the recombinant expression of some proteins [see, e.g., G. Ju et al., *Curr. Communic. in Mol. Biol.—Gene Transfer Vectors for Mammalian Cells*, C.S.H.L. Press (1987) pps. 39–45; and A. E. Atkinson et al., *Pestic. Sci.*, 28:215–224 (1990)].

There remains a need in the art for a method of increasing the efficiency of proteolytic processing of precursor polypeptides in recombinant host cells.

SUMMARY OF THE INVENTION

In one aspect, the present invention provides a selected host cell comprising a recombinant polynucleotide encoding PACE, which cell is capable of expressing PACE. In various embodiments of this aspect of the invention, the host cell may be a microorganism, e.g., a bacterial or fungal cell, a mammalian cell or an insect cell.

In a further aspect, the invention provides a selected host cell comprising a recombinant polynucleotide encoding PACE and a heterologous polynucleotide encoding a selected precursor polypeptide. The selected precursor polypeptide is preferably a substrate for the encoded PACE. This host cell is characterized by the ability to express both PACE and the heterologous precursor protein, which is then cleaved by the co-expressed PACE into its mature form. This host cell is thereby capable of producing high levels of PACE and the active, mature heterologous protein. In various embodiments of this aspect of the invention, the host cell may be a microorganism, e.g., a bacterial or fungal cell, a mammalian cell or an insect cell.

In another aspect, the present invention provides a recombinant expression vector or DNA molecule comprising a polynucleotide sequence encoding PACE or a homolog thereof. The vector preferably provides the sequence encoding PACE operably linked to a regulatory sequence capable of directing the replication and expression of PACE in a selected host cell.

In still another aspect, the recombinant expression vector or a DNA molecule of this invention further comprises a polynucleotide sequence encoding a precursor polypeptide, which is a substrate for PACE. The coding sequences of the vector are operably linked with one or more suitable regulatory sequences capable of directing the replication and expression of PACE and the selected propeptide in a selected host cell.

In still a further aspect the invention provides a method for expressing PACE in a selected host cell, described above, which comprises culturing the selected cell comprising a PACE-encoding polynucleotide under conditions suitable for expressing PACE.

In yet another aspect the invention provides a method for expressing PACE and a heterologous polypeptide in a selected host cell which comprises culturing a selected above-described cell comprising a PACE polynucleotide and a heterologous polynucleotide encoding a selected precursor polypeptide under suitable conditions permitting expression of both PACE and the heterologous polypeptide. This method may increase the efficiency of, or otherwise enhance the production of, a functional, mature protein, which protein requires processing by the enzyme PACE of a propeptide form for biological activity. The invention may also be used for the processing of γ-carboxylated proteins and other proteins not requiring gamma carboxylation, leading to higher levels of biologically active or otherwise useful proteins.

The method may involve transforming a selected host cell with the recombinant expression vectors described above.

This cell line is then cultured under appropriate conditions permitting expression of the recombinant protein(s). The expressed selected protein(s) is then harvested from the host cell or culture medium by suitable conventional means.

Other aspects and advantages of this invention are apparent from the following detailed description of the invention.

DESCRIPTION OF THE DRAWING

FIGS. 1A–1F [SEQ ID NO: 1] illustrates the published fur DNA sequence of A. M. W. van den Ouweland et al, *Nucl. Acids Res.*, 18(3):664 (1990).

FIGS. 2A–2F [SEQ ID NO: 3] illustrates the composite cDNA sequence encoding PACE, and the amino acids encoded therein, which differs from the above FIG. 1 in the inclusion of the 5' untranslated region from nucleotide #–320 to –1, and the 3' untranslated region from nucleotide #2383 to 3974.

DETAILED DESCRIPTION OF THE INVENTION

The present invention includes compositions (e.g., vectors, transformed host cells, recombinant polypeptides) and methods for producing, expressing, and also secreting, in selected host cells a mammalian endopeptidase, PACE, which is involved in the production of mature polypeptides from precursor polypeptides by cleavage at pairs of basic amino acids (-LysArg-, -LysLys-, and -ArgArg-). The compositions of the present invention, e.g., the recombinant polynucleotides, can be used for enhanced intracellular or extracellular production of PACE in various host cells, including microorganisms, e.g, bacteria and fungi; insect cells and mammalian cells. The production of PACE in these expression systems provides another embodiment of this invention, methods for the efficient processing and conversion of co-expressed heterologous precursor polypeptides having processing sites recognized by the PACE endopeptidase to desired mature forms of those polypeptides. The compositions of this invention are also useful for the production of the endopeptidase in high yields for production of purified endopeptidase for commercial purposes.

The practice of the present invention employs, unless otherwise indicated, conventional techniques of molecular biology, microbiology, recombinant DNA, and immunology, which are within the skill of the art. Such techniques are explained fully in the literature. See, e.g., Sambrook, et al., "Molecular Cloning; A Laboratory Manual", 2nd ed. (1989); "DNA Cloning", Vols. I and II (D. N Glover ed. 1985); "Oligonucleotide Synthesis" (M. J. Gait ed. 1984); "Nucleic Acid Hybridization" (B. D. Hames & S. J. Higgins eds. 1984); "Transcription and Translation" (B. D. Hames & S. J. Higgins eds. 1984); "Animal Cell Culture" (R. I. Freshney ed. 1986); "Immobilized Cells and Enzymes" (IRL Press, 1986); B. Perbal, "A Practical Guide to Molecular Cloning" (1984); the series, *Methods in Enzymology* (Academic Press, Inc.), particularly Vols. 154 and 155 (Wu and Grossman, and Wu, eds., respectively); "Gene Transfer Vectors for Mammalian Cells" (J. H. Miller and M. P. Calos eds. 1987, Cold Spring Harbor Laboratory); "Immunochemical Methods in Cell and Molecular Biology", Mayer and Walker, eds. (Academic Press, London, 1987); Scopes, "Protein Purification: Principles and Practice", 2nd ed. 1987 (Springer-Verlag, N.Y.); and "Handbook of Experimental Immunology", Vols. I–IV (D. M. Weir and C. C. Blackwell eds 1986). All patents, patent applications, and publications cited in the background and specification are incorporated herein by reference.

The following definitions may be applied to terms employed in the description of embodiments of the invention. As used herein, the term "PACE" is an acronym for paired basic amino acid converting (or cleaving) enzyme. PACE, originally isolated from a human liver cell line, is a subtilisin-like endopeptidase, i.e., a propeptide-cleaving enzyme which exhibits specificity for cleavage at basic residues of a polypeptide, e.g., -Lys-Arg-, -Arg-Arg, or -Lys-Lys-. PACE is stimulated by calcium ions; and inhibited by phenylmethyl sulfonyl fluoride (PMSF). A DNA sequence encoding PACE (or furin) was published in A. M. W. van den Ouweland et al, cited above, and appears in FIG. 1 [SEQ ID NO: 1].

A cDNA encoding at least one form of PACE, derived from an animal cell, more specifically from a human cell, is presented in FIG. 2 [SEQ ID NO: 3]. It is anticipated that other forms of PACE exist or that they can be created. PACE, as described herein, may be encoded by DNA sequences that differ in sequence from the published sequence and the sequence of FIG. 2 [SEQ ID NO: 3] due to natural allelic or species variations. Thus, the term "PACE" refers to any of the naturally occurring forms of PACE, including the PACE precursor shown in FIG. 2 [SEQ ID NO: 3] and various processed forms, including the mature PACE polypeptide.

Similarly the term PACE may include fragments of the PACE DNA and amino acid sequences or deliberately modified sequences thereof that maintain the catalytic specificity of that enzyme. Therefore, provided that the biological activities of mediating propeptide cleavage and/or γ-carboxylation are retained in whole or part despite such modifications, this invention encompasses the use of all such DNA sequences. The term "PACE" as used herein thus encompasses the peptide and DNA sequences specifically disclosed herein as well as analogs thereof retaining PACE biological activity.

Analogs of PACE included within the definition may include truncated polypeptides (including fragments) and PACE-like polypeptides, e.g., mutants, that retain catalytic activity and preferably have a homology to FIG. 1 [SEQ ID NO: 1] or 2 [SEQ ID NO: 3] of at least 80%, more preferably 90%, and most preferably 95%. Typically, such analogs differ by only 1, 2, 3, or 4 codon changes. Examples include polypeptides with minor amino acid variations from the natural amino acid sequence of PACE; in particular, conservative amino acid replacements. Conservative replacements are those that take place within a family of amino acids that are related in their side chains. Genetically encoded amino acids are generally divided into four families: (1) acidic=aspartate,. glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on the enzymatic activity, especially if the replacement does not involve an amino acid at the active site of the PACE-like polypeptide.

Utilizing the sequence data in FIG. 2 [SEQ ID NO: 3], as well as the denoted characteristics of PACE, it is within the skill of the art to obtain other DNA sequences encoding PACE. For example, the structural gene may be manipulated by varying individual nucleotides, while retaining the correct amino acid(s), or varying the nucleotides, so as to modify the amino acids, without loss of enzymatic activity. Nucleotides may be substituted, inserted, or deleted by known techniques, including, for example, in vitro mutagenesis and primer repair.

The structural gene may be truncated at its 3'-terminus and/or its 5'-terminus while retaining its endopeptidase activity. For example, PACE as encoded in FIG. 2 [SEQ ID NO: 3] contains a putative transmembrane domain which may serve to anchor it in the membranes of the Golgi in the cell in which it is expressed. Additionally, it may be desirable to delete the transmembrane (TM) region and/or the cysteine-rich region (CRR). It also may be desirable to remove the region encoding the signal sequence, and/or to replace it with a heterologous sequence.

It may also be desirable to ligate a portion of the PACE sequence (particularly that which includes the catalytic domain) to a heterologous. coding sequence, and thus to create a fusion peptide with the enzymatic specificity of PACE.

In addition to the above, other open reading frames (ORFS) or structural genes encoding PACE may be obtained and/or created from cDNA libraries from other animal cell sources.

As used herein, the term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The term "precursor polypeptide" denotes an expressed polypeptide which normally undergoes one or more post-translational proteolytic cleavages to yield a biologically active mature polypeptide. Included within the term "precursor polypeptide" are "prepropolypeptides" and "propolypeptides."

A "prepeptide" is the portion of a precursor polypeptide which is removed by "signal peptidase" cleavage during translocation of the polypeptide into the endoplasmic reticulum. The "prepeptide" region is usually at or near the amino terminus.

A "propeptide" is the portion of a precursor polypeptide which is removed by a "propolypeptide convertase" or "endopeptidase" (for example, Kex2 and PACE) during the maturation process of the polypeptide. Many proteins, such as plasma proteins, hormones, neuropeptides, and growth factors, are translated with an additional "propeptide" region located to the carboxy side of the prepeptide region. After cleavage of the prepeptide, the "propeptide" segment is cleaved by a site-specific endopeptidase contributing to the maturation of the polypeptide. A "mature" form of a polypeptide has had a prepeptide and/or propeptide region removed.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

A recombinant or derived polypeptide is not necessarily translated from a designated nucleic acid sequence, for example, the sequence in FIG. 2 [SEQ ID NO: 3]. It may be generated in any manner, including for example, chemical synthesis, or expression of a recombinant expression system, or isolation from a cell. A recombinant or derived polypeptide may include one or more analogs of amino acids or unnatural amino acids in its sequence. Methods of inserting analogs of amino acids into a sequence are known in the art. It also may include one or more labels, which are known to those of skill in the art.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog. Other known modifications include internucleotide modifications, for example, those with uncharged linkages (methyl phosphonates, phosphotriesters, phosphoamidates, carbamates, etc.) and with charged linkages (phosphorothioates, phosphorodithioates, etc.), those containing pendant moieties, such as, proteins (including nucleases, toxins, antibodies, signal peptides, poly-L-lysine, etc.), those with intercalators (acridine, psoralen, etc.), those containing chelators (metals, radioactive metals, boron, oxidative metals, etc.), those containing alkylators, those with modified linkages (alpha anomeric nucleic acids, etc.), as well as unmodified forms of the polynucleotide.

A "replicon" is any genetic element that behaves as an autonomous unit of polynucleotide replication within a cell, that is, capable of replication under its own control. Thus a replicon may include, without limitation, a selectable marker, a plasmid, a chromosome, a virus, a cosmid.

A "vector" is a replicon in which another polynucleotide segment is attached, so as to bring about the replication and/or expression of the attached segment.

A "Control sequence" or "Regulatory sequence" refers to polynucleotide sequences which are necessary to effect the replication and expression of coding sequences to which they are ligated. The nature of such control sequences differs depending upon the host organism. In prokaryotes, such control sequences generally include promoter, ribosomal binding site, and transcription termination sequences. In eukaryotes, generally, such control sequences include promoters and transcription termination sequences. The term "control sequences" is intended to include, at a minimum, all components whose presence is necessary for expression in a selected host cell, and may also include additional components whose presence is advantageous, for example, leader sequences and fusion partner sequences.

"Operably linked", or related terms such as "operative association", refer to the relationship between the components so described which permits them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide. This region may represent a portion of a coding sequence or a total coding sequence.

A "coding sequence" is a polynucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

"PCR" refers to the technique of polymerase chain reaction as described in Saiki et al., *Nature*, 324:163 (1986); U.S. Pat. No. 4,683,195; and U.S. Pat. No. 4,683,202. Other known PCR modifications are also included by use of this acronym.

As used herein, x is "heterologous" with respect to y if x is not naturally associated with y in the identical manner; i.e., x is not associated with y in nature or x is not associated with y in the same manner as is found in nature.

"Recombinant host cells", "host cells", "cells", "cell lines", "cell cultures", and other such terms denote selected host cells, e.g., mammalian, insect or microorganism cells, that can be, or have been, used as recipients for a recombinant vector or other transfer DNA. These terms include the progeny of the original cell which has been transformed. It is understood that the progeny of a single parental cell may not necessarily be completely identical in morphology or in genomic or total DNA complement as the original parent, due to natural, accidental, or deliberate mutation.

As used herein, the term "microorganism" includes prokaryotic and eukaryotic microbial species such as bacteria and fungi. Fungi include yeast and filamentous fungi. The term "microorganism" specifically excludes mammalian cells and insect cells.

"Mammalian cells" are cells that are from a member of the Class Mammalia, and specifically exclude microorganism cells and insect cells.

Insect cells and compatible vectors which are useful as recombinant expression systems are known in the art. Examples include insect expression and transfer vectors derived from the baculovirus *Autographa californica* nuclear polyhedrosis virus (hereinafter "AcNPV" or "baculovirus"), which is a helper-independent, viral expression vector. Viral expression vectors derived from this system usually use the strong viral polyhedrin gene promoter to drive expression of heterologous genes.

"Transformation", as used herein, refers to the insertion of an exogenous polynucleotide into a host cell, irrespective of the method used for the insertion. Examples include direct uptake, transfection, f-mating, transduction, infection or electroporation. The exogenous polynucleotide may be maintained as a non-integrated vector, for example, a plasmid, or alternatively, may be integrated into the host genome.

The inventors have discovered that the enzyme PACE may be recombinantly expressed in a variety of host cells, including mammalian cells, microorganisms and insect cells. One method of this invention employs a single transformed host cell expressing PACE. A polynucleotide sequence encoding PACE or a biologically active fragment thereof may be inserted into an expression vector and operably linked to expression control sequences suitable for expression of the enzyme in the selected host cell. Transformation or transfection of the vector into the selected host cell can be effected using materials and methods conventional for introducing polynucleotides into a host cell. Among such methods are packaging the polynucleotide in a virus and transducing a host cell with the virus or by transfection procedures known in the art, as exemplified by U.S. Pat. Nos. 4,399,216; 4,912,040; 4,740,461; 4,959,455 (these patents are incorporated herein by reference). The transformation procedure used depends upon the host to be transformed. Once the vector is transformed into the selected host cell, the cell is cultured to express PACE.

In order to obtain PACE expression, recombinant host cells derived from the transformants are incubated under conditions which allow expression of the recombinant PACE encoding sequence. These conditions will vary, dependent upon the host cell selected. However, the conditions are readily ascertainable to those of ordinary skill and knowledge in the art.

Detection of PACE expressed in the transformed host cell may be by several methods. For example, detection can be by enzymatic activity (or increased enzymatic activity or increased longevity of enzymatic activity) using fluorogenic substrates which are comprised of a dibasic cleavage site for which PACE is specific. PACE may also be detected by its immunological reactivity with anti-PACE antibodies.

PACE may be isolated from the cell by lysis, if formed intracellularly, or isolated from the culture medium, if secreted, by conventional methods. If the transmembrane domain is retained during expression so that the PACE localizes in the host cell membranes, the host cells may be lysed and the membrane fragments isolated by conventional techniques. These fragments containing enriched amounts of PACE may be used as is, or fixed to a solid substrate for use in processing precursor polypeptides. The cell membranes may be dispersed in a medium at optimal pH, or particle bound membrane may be packed in a column. Other useful configurations may also be employed.

Recombinantly expressed PACE can improve the efficiency of cleavage of a precursor polypeptide between the dibasic residues Lys-Arg, Lys-Lys or Arg-Arg into its mature form. Thus another embodiment of this invention is provided by the action of recombinantly-expressed PACE on selected precursor polypeptides, either recombinant or naturally occurring. The expressed precursor will be one which has a processing site recognized by PACE.

As one example, the recombinantly-expressed PACE may be used for the in vitro conversion of heterologous precursor polypeptides to mature polypeptides. Soluble recombinant PACE, i.e., a truncated PACE polypeptide lacking a transmembrane domain, may be used as an added reagent to extracellular (or conditioned) media where a precursor product is secreted from the cell in which it is expressed.

More preferably, the co-expression of PACE and a proprotein which requires such processing for production of the mature protein is an embodiment of this invention, which can result in high level expression of the mature protein. Additionally, the inventors have also surprisingly discovered that co-expression of PACE with proteins requiring γ-carboxylation for biological activity permits the expression of increased yields of functional, biologically active mature proteins in eukaryotic, preferably mammalian, cells.

Examples of precursor polypeptides for use in the present invention include, but are not limited to, transforming growth factor (TGF) beta and its superfamily, including inhibin and activin; bone morphogenic proteins (BMP); insulin and relaxin; coagulation factors, such as von Willebrand factor (vWF); Factor IX, Protein C, Protein S, Prothrombin Factor X, Factor VII and bone gamma-carboxyglutamate protein, growth factors, such as platelet derived growth factor (PDGF) and nerve growth factor (NGF); and virus polypeptides, including those from cytomegalovirus (CMV), hepatitis delta virus (HDV), hepatitis C virus (HCV), human immunodeficiency virus (HIV), and herpes simplex virus (HSV). Any precursor polypeptide with at least one dibasic cleavage site is a candidate for the present invention.

Methods for producing a desired mature polypeptide by co-expression with PACE can include the following techniques. First, a single vector containing coding sequences for both PACE and the heterologous precursor polypeptide can be inserted into a selected host cell. Alternatively, two separate vectors coding, respectively, for PACE and the heterologous precursor polypeptide, can be inserted into a host. Upon culturing under suitable conditions for the selected host cell, the two polypeptides are produced and interact to provide cleavage of the proprotein into the mature protein.

Another alternative is the use of two transformed host cells wherein one host cell expresses soluble recombinant PACE and the other host cell expresses the heterologous precursor polypeptide which will be secreted into the medium. These host cells can be co-cultured under conditions which allow expression and secretion or release of the recombinant PACE, as well as expression, secretion or release of the precursor polypeptide, and its cleavage into the mature form by the extracellular PACE. In this method, it is preferred that the PACE polypeptide lacks the transmembrane domain so that it secretes into the medium.

In some instances, it may be desirable to have a plurality of copies, two or more, of the gene expressing the expression product precursor in relation to the PACE gene, or vice versa. This can be achieved in a variety of ways. For example, one may use separate vectors or plasmids, where the vector containing the PACE encoding polynucleotide has a higher copy number than the vector containing the polynucleotide sequence encoding the heterologous precursor polypeptide, or vice versa. In this situation, it would be desirable to have different markers on the two plasmids, so as to ensure the continued maintenance of the plasmids in the host. Alternatively, one or both genes could be integrated into the host genome, and one of the genes could be associated with an amplifying gene, (e.g., dhfr or one of the metallothionein genes).

Alternatively, one could employ two transcriptional regulatory regions having different rates of transcriptional initiation, providing for the enhanced expression of either the PACE gene or the expression of the precursor polypeptide, relative to the other gene. As another alternative, one can use different promoters, where one promoter provides for a low level of constitutive expression of either PACE or the precursor polypeptide, while the second promoter provides for a high level of induced expression of the other product. A wide variety of promoters are known for the selected host cells, and can be readily selected and employed in the invention by one of skill in the art.

By use of these methods, the natural level of PACE may be greatly enhanced and/or the longevity of protease activity may be increased, so as to more efficiently process the expression product precursor.

A. Mammalian Expression of PACE

The methods of the present invention may be performed by inserting a polynucleotide sequence encoding PACE or a fragment thereof into a suitable mammalian expression vector. The vector containing PACE is then transformed into a selected mammalian cell line. The establishment of cell lines which express PACE provides a convenient and efficient mechanism for the high level production of PACE, as well as for the production of more completely processed and biologically active proteins.

Where the method involves the co-expression of PACE and a precursor polypeptide, a single vector can carry the PACE DNA and another vector can carry the selected precursor DNA, each under the control of a selected expression control sequence. Alternatively, both the PACE and precursor DNA sequences may be carried on a single recombinant vector molecule in which case they may be operably linked to respective expression control sequences or may share a common expression control sequence. As another alternative, a vector containing the PACE DNA may be transfected into a host cell line known to express the desired proprotein, or a vector containing the DNA for the desired protein may be transfected into a cell known to express PACE.

Vector construction employs techniques which are known in the art. Site-specific DNA cleavage involved in such construction is performed by treating with suitable restriction enzymes under conditions which generally are specified by the manufacturer of these commercially available enzymes.

A suitable expression vector is one that is compatible with the desired function (e.g., transient expression, long term expression, integration, replication, amplification) and in which the control elements are compatible with the host cell. In general, the vectors employed will contain selected regulatory sequences operably linked with the DNA coding sequences of PACE and selected precursor and capable of directing the replication and expression thereof in selected host cells.

Vectors suitable for replication in mammalian cells may include viral replicons, or sequences that ensure integration of the sequence encoding PACE into the host genome. Suitable vectors may include, for example, those derived from simian virus SV40, retroviruses, bovine papilloma virus, vaccinia virus, and adenovirus. The components of the vectors, e.g. replicons, selection genes, enhancers, promoters, and the like, may be obtained from natural sources or synthesized by known procedures. [See, Kaufman et al, *J. Mol. Biol.*, 159:511–521 (1982); and Kaufman, *Proc. Natl. Acad. Sci., USA*, 82:689–693 (1985)].

A suitable vector, for example, is one derived from vaccinia viruses. In this case, the heterologous DNA is inserted into the vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid shuttle vectors that greatly facilitate the construction of recombinant viruses have been described [see, for example, Mackett et al. (1984), Chakrabarti et al. (1985); Moss (1987)]. Expression of the heterologous polypeptide then occurs in cells or individuals which are immunized with the live recombinant vaccinia virus.

Suitable mammalian expression vectors usually contain one or more eukaryotic transcription units that are capable of expression in mammalian cells. The transcription unit is comprised of at least a promoter element to mediate transcription of foreign DNA sequences. Suitable promoters for mammalian cells are known in the art and include viral promoters such as that from simian virus 40 (SV40), cytomegalovirus (CMV), Rous sarcoma virus (RSV), adenovirus (ADV), and bovine papilloma virus (BPV).

In addition, the transcription unit may also be comprised of a termination sequence and poly(A) addition sequences which are operably linked to the PACE and/or precursor coding sequence(s). The transcription unit may also be comprised of an enhancer sequence which increases the expression of PACE and/or the precursor.

The optional presence of an enhancer element (enhancer), combined with the promoter elements described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when they are placed upstream or downstream from the transcription initiation site, in either normal or flipped orientation, or at a distance of more than 1000 nucleotides from the promoter [Maniatis et al. *Science*, 236:1237 (1987); Alberts et al., *Molecular Biology of the Cell*, 2nd ed. (1989)]. Enhancer elements derived from viruses may be particularly useful, because they typically have a broader host range. Examples include the SV40 early gene enhancer [Dijkema et al, *EMBO J.*, 4:761 (1985)] and the enhancer/promoters derived from the long terminal repeat (LTR) of the Rous Sarcoma Virus [Gorman et al., *Proc. Natl. Acad. Sci.* 79:6777 (1982b)] and from human cytomegalovirus [Boshart et al., *Cell*, 41:521 (1985)]. Additionally, some enhancers are regulatable and become active only in the presence of an inducer, such as a hormone or metal ion [Sassone-Corsi and Borelli, *Trends Genet.* 2:215 (1986); Maniatis et al. *Science*, 236:1237 (1987)].

Sequences which cause amplification of the gene may also be desirable, as are sequences which encode selectable markers. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

Alternatively, the vector DNA may include all or part of the bovine papilloma virus genome [Lusky et al, *Cell*, 36:391–401 (1984)] and be carried in cell lines such as C127 mouse cells as a stable episomal element.

The vector used in the examples below is pMT3, a derivative of the previously described vector pMT2 [R. Kaufman, *Mol. Cell. Biol.*, 9:946–958 (1989)]. One skilled in the art can also construct other mammalian expression vectors comparable to the pMT3/PACE vector (see Example 1) by, e.g. inserting the DNA sequence of PACE from pMT3 into another vector, such as pJL3, pJL4 [Gough et al., *EMBO J.*, 4:645–653 (1985)], employing well-known recombinant genetic engineering techniques. The mammalian cell expression vectors described herein may be synthesized by techniques well known to those skilled in this art. Other appropriate expression vectors of which numerous types are known in the art for mammalian expression can also be used for this purpose.

One or more selected vector(s) encoding PACE and/or the precursor polypeptide can be used for transformation of a suitable mammalian host cell. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC). Exemplary mammalian host cells include particularly primate cell lines and rodent cell lines, including transformed cell lines. Preferably for stable integration of the vector DNA, and for subsequent amplification of the integrated vector DNA, both by conventional methods, Chinese hamster ovary (CHO) cells are employed as a mammalian host cell of choice. Other suitable cell lines include, but are not limited to, HeLa cells, baby hamster kidney (BHK) cells, monkey kidney cells (COS-1), human hepatocellular carcinoma cells (e.g., Hep G2), human adenovirus transformed 293 cells, mouse L-929 cells, HaK hamster cell lines, murine 3T3 cells derived from Swiss, Balb-c or NIH mice and a number of other cell lines. Another suitable mammalian cell line is the CV-1 cell line. Normal diploid cells, cell strains derived from in vitro culture of primary tissue, as well as primary explants, are also suitable. Candidate cells may be genotypically deficient in the selection gene, or may contain a dominantly acting selection gene.

The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446.

The host cells transformed with the one or more vectors carrying the PACE DNA and the selected precursor DNA are selected, e.g. by conventional means, and may then be cultured under suitable conditions if desired, with amplification of one or both introduced genes. The method of this present invention therefore comprises culturing a suitable cell or cell line, which has been transformed with a DNA sequence coding for PACE and a DNA sequence coding for the selected precursor, each coding sequence under the control of a transcriptional regulatory sequence. The expressed mature protein is then recovered, isolated and purified from the culture medium (or from the cell, if expressed intracellularly) by appropriate means known to one of skill in the art.

With respect to γ-carboxylated proteins, it is presently and theoretically contemplated that the expression of PACE in mammalian cells increases the efficiency of γ-carboxylation, a post-translational modification required for biological activity of certain mature proteins. The method is especially useful in the processing of vitamin K-dependent blood coagulation proteins. More specifically the method is useful in processing and γ-carboxylating other proteins including Protein C, Protein S, Prothrombin Factor IX, Factor VII, Factor X and bone γ-carboxyglutamate protein. For example, co-expression with PACE with such a propeptide permits high level recombinant expression of biologically active mature proteins.

In addition, high levels of recombinant expression of functional proteins can also be achieved by use of the present method by expressing PACE with more completely processed proteins expressed from other genes. For example, coexpression of PACE with non-Vitamin K dependent propeptides which require cleavage, but not γ-carboxylation, for biological activity may produce high yields of functional mature proteins.

One such protein which may be expressed in high functional yields by the present method is bone morphogenic protein (BMP), particularly BMP-2 [see, e.g., E. Wang et al, *Proc. Natl. Acad. Sci. USA*, 87:2220–2224 (1990), which is incorporated by reference herein for information about that protein). Other such proteins which may be produced in high functional yields by the present invention include tumor growth factor β (TGF-β) and platelet-derived growth factor (PDGF) and the precursors identified specifically above.

Further, the present invention also encompasses the use of recombinant-derived PACE for in vitro processing of nerve growth factor and monobasic propiomelanocortin. PACE may also be useful in the processing of proteins, such as insulin, and for the maturation of viruses, such as HIV and Hepatitis C, which also require precursor processing at paired basic amino acid residues.

While mammalian cells are preferred as hosts for the co-expression of PACE and a mammalian proprotein, it is anticipated that microorganism and insect cells may be suitable hosts for such expression of PACE and mammalian proproteins, as well as expression, where desired of proproteins of microbial or insect origin.

B. Expression of PACE in Microorganism Cells

The PACE gene or a fragment thereof can be expressed in a eukaryotic or prokaryotic microorganism system, such as fungi, including yeast, or bacteria. Fragments can include truncated forms of the PACE gene. Examples of truncation include, but are not limited to, deletion of the transmembrane region and/or the cysteine-rich region.

Fungal expression systems can utilize both yeast and filamentous fungi hosts. Examples of filamentous fungi expression systems are Aspergillus, as described in EPO Pub. No. 357 127 (published Mar. 7, 1990), and *Acremonium chrysogenum*, described in EPO Pub. No. 376 266 (published Jul. 4, 1990).

A yeast expression system can typically include one or more of the following: a promoter sequence, fusion partner sequence, leader sequence, transcription termination sequence. These elements can be combined into an expression cassette, which may be maintained in a replicon, preferably with a selectable marker.

A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (E.P.O. Pub. No. 284044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (E.P.O. Pub. No. 329203). The yeast PHO5 gene, encoding acid phosphatase, also provides useful promoter sequences [Myanohara et al., *Proc. Natl. Acad. Sci. USA*, 80:1 (1983)).

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region [U.S. Pat. Nos. 4,876,197 and 4,880,734]. Other examples of hybrid promoters include promoters which consist of the regulatory sequences of either the ADH2, GAL4, GAL10, or PHO5 genes, combined with the transcriptional activation region of a glycolytic enzyme gene such as GAP or PyK [E.P.O. Pub. No. 164556]. Furthermore, a yeast promoter can include naturally occurring promoters of non-yeast origin that have the ability to bind yeast RNA polymerase and initiate transcription. Examples of such promoters include, inter alia, [Cohen et al., *Proc. Natl. Acad. Sci. USA*, 77:1078 (1980); Henikoff et al., *Nature* 283:835 (1981); Hollenberg et al., *Curr. Topics Microbiol. Immunol.*, 96:119 (1981); Hollenberg et al., "The Expression of Bacterial Antibiotic Resistance Genes in the Yeast Saccharomyces cerevisiae," in: *Plasmids of Medical, Environmental and Commercial Importance* (eds. K. N. Timmis and A. Puhler, 1979); Mercerau-Puigalon et al., *Gene*, 11:163 (1980); and Panthier et al., *Curr. Genet.*, 2:109 (1980)].

The PACE gene or a fragment thereof may be expressed intracellularly in yeast. A promoter sequence may be directly linked with the PACE gene or fragment, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Intracellularly expressed fusion proteins provide an alternative to direct expression of the PACE gene or fragment. Typically, a DNA sequence encoding the N-terminal portion of a stable protein, a fusion partner, is fused to the 5' end of heterologous DNA encoding the desired polypeptide. Upon expression, this construct will provide a fusion of the two amino acid sequences. For example, the yeast or human superoxide dismutase (SOD) gene, can be linked at the 5' terminus of the PACE gene or fragment thereof and expressed in yeast. The DNA sequence at the junction of the two amino acid sequences may or may not encode a cleavable site. See, e.g., E.P.O. Pub. No. 196056. Another example is a ubiquitin fusion protein. Such a ubiquitin fusion protein preferably retains a site for a processing enzyme (e.g. ubiquitin-specific processing protease) to cleave the ubiquitin from the PACE polypeptide. Through this method, therefore, a mature PACE polypeptide can be isolated [see, P.C.T. WO 88/024066].

Alternatively, PACE polypeptides can also be secreted from the cell into the growth media by creating chimeric DNA molecules that encode a fusion protein comprised of a leader sequence fragment that provides for secretion in yeast of the PACE polypeptides. Preferably, there are processing sites encoded between the leader fragment and the PACE gene or fragment thereof that can be cleaved either in vivo or in vitro. The leader sequence fragment typically encodes a signal peptide comprised of hydrophobic amino acids which direct the secretion of the protein from the cell.

DNA encoding suitable signal sequences can be derived from genes for secreted yeast proteins, such as the yeast invertase gene [E.P.O. Pub. No. 12873; J.P.O. Pub. No.

62,096,086] and the A-factor gene (U.S. Pat. No. 4,588, 684]. Alternatively, leaders of non-yeast origin, such as an interferon leader, exist that also provide for secretion in yeast [E.P.O. Pub. No. 60057].

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) [U.S. Pat. Nos. 4,546,083 and 4,870,008; and E.P.O. Pub. No. 324274]. Additional leaders employing an alpha-factor leader fragment that provides for secretion include hybrid alpha-factor leaders made with a presequence of a first yeast, but a pro-region from a second yeast alphafactor. See, e.g., P.C.T. WO 89/02463.

Typically, transcription termination sequences recognized by yeast-are regulatory regions located 3' to the translation stop codon and thus, together with the promoter, flank the coding sequence. These sequences direct the transcription of an mRNA which can be translated into the polypeptide encoded by the DNA. Examples of transcription terminator sequence and other yeast-recognized termination sequences, such as those coding for glycolytic enzymes, are known to those of skill in the art.

Typically, the above described components, comprising a promoter, leader (if desired), coding sequence of interest, and transcription termination sequence, are put together into expression constructs. Expression constructs or cassettes are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 [Botstein et al., *Gene*, 8:17–24 (1979)], pCl/1 [Brake et al., *Proc. Natl. Acad. Sci USA*, 81:4642–4646 (1984)], and YRp17 (Stinchcomb et al., *J. Mol. Biol.*, 158:157 (1982)]. In addition, a replicon may be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Enter a high or low copy number vector may be selected, depending upon the effect on the host of the vector and the PACE polypeptides. See e.g., Brake et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al., *Methods in Enzymol.*, 101:228–245 (1983)]. An integrating vector may be directed to a specific locus in yeast by selecting the appropriate homologous sequence for inclusion in the vector. See Orr-Weaver et al., supra. One or more expression constructs may integrate, possibly affecting levels of recombinant protein produced [Rine et al., *Proc. Natl. Acad. Sci. USA*, 80:6750 (1983)]. The chromosomal sequences included in the vector can occur either as a single segment in the vector, which results in the integration of the entire vector, or as two segments homologous to adjacent segments in the chromosome and flanking the expression construct in the vector, which results in the stable integration of only the expression construct.

Typically, extrachromosomal and integrating expression vectors may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al., *Microbiol. Rev.*, 51:351 (1987)].

Alternatively, some of the above described components can be put together into transformation vectors. Transformation vectors are typically made up of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: Candida albicans [Kurtz, et al., *Mol. Cell. Biol.*, 6:142 (1986)], Candida maltosa [Kunze et al., *J. Basic Microbiol.*, 25:141 (1985)]; Hansenula polymorpha [Gleeson et al., *J. Gen. Microbiol.* 132:3459 (1986); Roggenkamp et al., *Mol. Gen. Genet.* 202:302 (1986)]; Kluyveromyces fragilis [Das et al., *J. Bacteriol.* 158:1165 (1984)]; Kluyveromyces lactis [De Louvencourt et al., *J. Bacteriol.* 154:737 (1983); Van den Berg et al., *Bio/Technology* 8:135 (1990)]; Pichia guillerimondii [Kunze et al., *J. Basic Microbiol.* 25:141 (1985)]; Pichia pastoris [Cregg et al., *Mol. Cell. Biol.* 5:3376 (1985); U.S. Pat. Nos. 4,837,148 and 4,929,555]; Saccharomyces cerevisiae [Hinnen et al., *Proc. Natl. Acad. Sci. USA* 75:1929 (1978); Ito et al., *J. Bacteriol.* 153:163 (1983)]; Schizosaccharomyces pombe [Beach and Nurse, *Nature* 300:706 (1981)]; and Yarrowia lipolytica [Davidow, et al., *Curr. Genet.* 10:380471 (1985); and Gaillardin et al., *Curr. Genet.* 10:49 (1985)).

Methods of introducing exogenous DNA into yeast hosts are well-known in the art, and typically include either the transformation of spheroplasts or of intact yeast cells treated with alkali cations. Transformation procedures usually vary with the yeast species to be transformed. See e.g., Kurtz et al., *Mol. Cell. Biol.* 6:142 (1986); Kunze et al., *J. Basic Microbiol.* 25:141 (1985) for Candida. See, e.g., Gleeson et al., *J. Gen. Microbiol.* 132:3459 (1986); Roggenkamp et al., *Mol. Gen. Genet.* 202:302 (1986) for Hansenula. See, e.g., Das et al., *J. Bacteriol.* 158:1165 (1984); De Louvencourt et al., *J. Bacteriol.* 154:1165 (1983); Van den Berg et al., *Bio/Technology* 8:135 (1990) for Kluyveromyces. See, e.g., Cregg et al., *Mol. Cell. Biol.* 5:3376 (1985); Kunze et al., *J. Basic Microbiol.* 25:141 (1985); U.S. Pat. Nos. 4,837,148 and 4,929,555 for Pichia. See, e.g., Hinnen et al., *Proc. Natl. Acad. Sci. USA* 75:1929 (1978); Ito et al., *J. Bacteriol.* 153:163 (1983) for Saccharomyces. See, e.g., Beach and Nurse, *Nature* 300:706 (1981) for Schizosaccharomyces. See, e.g., Davidow et al., *Curr. Genet.* 10:39 (1985); Gaillardin et al., *Curr. Genet.* 10:49 (1985) for Yarrowia.

Additionally, the PACE gene or a fragment thereof can be expressed in a bacterial system. Therein, a bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* [Raibaud et al., *Annu. Rev. Genet.* 18:173 (1984)]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., *Nature* 198:1056 (1987)], and maltose. Additional examples include promoter sequences derived from biosynthetic enzymes such as tryptophan (trp) [Goeddel et al., *Nuc. Acids Res.* 8:4057 (1980); Yelverton et al., *Nucl. Acids Res.* 9:731 (1981); U.S. Pat. No. 4,738,921; E.P.O. Pub. Nos. 36,776 and 121,775]. The β-lactomase (bla) promoter system [Weissmann, "The Cioning of Interferon and Other Mistakes" in *Interferon* 3 (ed. I. Gresser, 1981)]; bacteriophage lambda PL [Shimatake et al., *Nature* 292:128 (1981)] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433]. For example, the tac promoter is a hybrid trp-lac promoter comprised of both trp promoter and lac operon sequences that is regulated by the lac repressor [Amann et al., *Gene* 25:167 (1983); de Boer et al., *Proc. Natl. Acad. Sci.* 80:21 (1983)]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., *J. Mol. Biol.* 189:113 (1986); Tabor et al., *Proc Natl. Acad. Sci.* 82:1074 (1985)]. In addition, a hybrid promoter can also be comprised of a bacteriophage promoter and an *E. coli* operator region (E.P.O. Pub. No. 267,851].

In addition to a functioning promoter sequence, an efficient ribosome binding site is also useful for the expression of the PACE gene or fragment thereof in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon [Shine et al., *Nature* 254:34 (1975)]. The SD sequence is thought to promote binding of mRNA to the ribosome by the pairing of bases between the SD sequence and the 3' and of *E. coli* 16S rRNA [Steitz et al., "Genetic signals and nucleotide sequences in messenger RNA" in *Biological Regulation and Development: Gene Expression* (ed. R. F. Goldberger, 1979)]. To express eukaryotic genes and prokaryotic genes with weak ribosome-binding site [Sambrook et al., "Expression of cloned genes in *Escherichia coli*" in *Molecular Cloning: A Laboratory Manual*, cited above].

PACE may be expressed intracellularly. A promoter sequence may be directly linked with the PACE gene or a fragment thereof, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase [E.P.O. Pub. No. 219,237].

Fusion proteins provide an alternative to direct expression. Typically, a DNA sequence encoding the N-terminal portion of an endogenous bacterial protein, or other stable protein, is fused to the 5' end of heterologous PACE coding sequences. Upon expression, this construct will provide a fusion of the two amino acid sequences. For example, the bacteriophage lambda cell gene can be linked at the 5' terminus of the PACE gene or fragment thereof and expressed in bacteria. The resulting fusion protein preferably retains a site for a processing enzyme (factor Xa) to cleave the bacteriophage protein from the PACE gene or fragment thereof [Nagai et al., *Nature* 309:810 (1984)].

Fusion proteins can also be made with sequences from the lacZ [Jia et al., *Gene* 60:197 (1987)], trpE [Allen et al., *J. Biotechnol.*, 5:93 (1987); Makoff et al., *J. Gen. Microbiol.* 135:11 (1989), and Chey [E.P.O. Pub. No. 324,647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the PACE polypeptide. Through this method, mature PACE polypeptides can be isolated [Miller et al., *Bio/Technology*, 7:698 (1989)].

Alternatively, PACE polypeptides can also be secreted from the cell by creating chimeric DNA molecules that encode a fusion protein comprised of a signal peptide sequence fragment that provides for secretion of the PACE polypeptides in bacteria [U.S. Pat. No. 4,336,336]. The signal sequence fragment typically encodes a signal peptide comprised of hydrophobic amino acids which direct the secretion of the protein from the cell. The protein is either secreted into the growth media (Gram-positive bacteria) or into the periplasmic space, located between the inner and outer membrane of the cell (gram-negative bacteria). Preferably there are processing sites, which can be cleaved either in vivo or in vitro, encoded between the signal peptide fragment and the PACE polypeptide.

DNA encoding suitable signal sequences can be derived from genes for secreted bacterial proteins, such as the *E. coli* outer membrane protein gene (ompA) [Masui et al., in *Experimental Manipulation of Gene Expression* (1983); Ghrayeb et al., *EMBO J.* 3:2437 (1984)] and the *E. coli* alkaline phosphatase signal sequence (phoA) [Oka et al., *Proc. Natl. Acad. Sci.* 82:7212 (1985)]. As an additional example, the signal sequence of the alpha-amylase gene from various Bacillus strains can be used to secrete heterologous proteins from *B. subtilis* [Palva et al., *Proc. Natl. Acad. Sci. USA* 79:5582 (1982); E.P.O. Pub. No. 244,042].

Typically, transcription termination sequences recognized by bacteria are regulatory regions located 3' to the translation stop codon and thus, together with the promoter, flank the coding sequence. These sequences direct the transcription of an mRNA which can be translated into the polypeptide encoded by the DNA. Transcription termination sequences frequently include DNA sequences (of about 50 nucleotides) which are capable of forming stem loop structures that aid in terminating transcription. Examples include transcription termination sequences derived from genes with strong promoters, such as the trp gene in *E. coli* as well as other biosynthetic genes.

Typically, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The description of similar replicon systems, including copy number parameters are described in detail above in connection with yeast expression systems. Such description is also applicable to bacterial systems.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome [E.P.O. Pub. No. 127, 328]. Integrating vectors may also be comprised of bacteriophage or transposon sequences.

Typically, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al., *Annu. Rev.Microbiol.* 32:469 (1978)]. Selectable markers may also include biosynthetic genes, such as those in the histidine, tryptophan, and leucine biosynthetic pathways.

Alternatively, some of the above described components can be put together in transformation vectors. Transformation vectors are typically comprised of a selectable market that is either maintained in a replicon or developed into an integrating vector, as described above.

Expression and transformation vectors, either extrachromosomal replicons or integrating vectors, have been developed for transformation into many bacteria. For example, expression vectors have been developed for the following bacteria: *Bacillus subtilis* [Palva et al., *Proc. Natl. Acad. Sci. USA* 79:5582 (1982); E.P.O. Pub. Nos. 36,259 and 63,953; P.C.T. WO 84/04541]; *E. coli* [Shimatake et al., *Nature*, 292:128 (1981); Amann et al., *Gene*, 40:183 (1985); Studier et al., *J. Mol. Biol.* 189:113 (1986); E.P.O. Pub. Nos. 36,776, 136,829 and 136,907; U.K. Patent Application Serial No. 8418273]; *Streptococcus cremoris* [Powell et al., *Appl. Environ. Microbiol.* 54:655 (1988)]; *Streptococcus lividans* [Powell et al., *Appl. Environ. Microbiol.* 54:655 (1988)]; *Streptomyces lividans* [U.S. Pat. No. 4,745,056].

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., [Masson et al., *FEMS Microbiol. Lett.* 60:273 (1989); Palva et al., *Proc. Natl. Acad. Sci. USA* 79:5582 (1982); E.P.O. Pub. Nos. 36,259 and 63,953; P.C.T. WO 84/04541, Bacillus], [Miller et al., *Proc. Natl. Acad. Sci.* 85:856 (1988); Wang et al., *J. Bacteriol.* 172:949 (1990) for Campylobacter]; [Cohen et al., *Proc. Natl. Acad. Sci.* 69:2110 (1973); Dower et al., *Nucleic Acids Res.* 16:6127 (1988); Kushner, "An improved method for transformation of *Escherichia coli* with ColE1-derived plasmids" in *Genetic Engineering: Proceedings of the International Symposium on Genetic Engineering* (eds. H. W. Boyer and S. Nicosia, 1978); Mandel et al., *J. Mol. Biol.* 53:159 (1970); Taketo, *Biochim. Biophys. Acta* 949:318 (1988) for Escherichia], [Chassy et al., *FEMS Microbiol. Lett.* 44:173 (1987) for Lactobacillus]; [Fiedler et al., *Anal. Biochem* 170:38 (1988) for Pseudomonas]; [Augustin et al., *FEMS Microbiol. Lett.* 66:203 (1990) for Staphylococcus]; [Barany et al., *J. Bacteriol.* 144:698 (1980); Harlander, "Transformation of *Streptococcus lactis* by electroporation," in *Streptococcal Genetics* (ed. J. Ferretti and R. Curtiss III, 1987); Perry et al., *Infec. Immun.* 32:1295 (1981); Powell et al., *Appl. Environ. Microbiol.* 54:655 (1988); Somkuti et al., *Proc. 4th Evr. Cong. Biotechnology* 1:412 (1987) for Streptococcus].

C. Expression in Insect Cells

In one aspect of the invention, enhanced processing of a precursor polypeptide to a mature polypeptide is achieved by introducing into an insect host cell DNA sequences coding for PACE, yielding a recombinant insect cell. The precursor polypeptide and PACE are related in that the precursor has at least one selectively cleavable peptide bond, which is cleavable by PACE. The transcriptional initiation and expression of PACE allows for an enhanced production of PACE as compared to the unmodified host.

The polynucleotide encoding PACE is inserted into a suitable insect expression vector, and is operably linked to the control elements within that vector. Vector construction employs techniques which are known in the art. Various constructs can be prepared once the desired PACE DNA sequence is obtained.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector, which allows for the homologous recombination of the heterologous gene into the baculovirus genome, and appropriate insect host cells and growth media.

After inserting the PACE DNA sequence into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego, Calif. ("MaxBac" kit). These techniques are generally known to those skilled in the art and fully described in Summers and Smith, *Texas Agricultural Experiment Station Bulletin No. 1555* (1987) (hereinafter "Summers and Smith"), and incorporated by reference.

Prior to inserting the PACE DNA sequence into the baculovirus genome, the above described components, comprising a promoter, leader (if desired), coding sequence of interest, and transcription termination sequence, are typically assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT [see, e.g., Luckow and Summers, *Virology*, 17:31 (1989)].

The plasmid usually also contains the polyhedrin polyadenylation signal [Miller et al., *Ann. Rev. Microbiol.*, 42:177 (1988) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein [Friesen et al., "The Regulation of Baculovirus Gene Expression," in *The Molecular Biology of Baculoviruses* (ed. Walter Doerfler, 1986); E.P.O. Pub. Nos. 127,839 and 155,476]; and the gene encoding the p10 protein [Vlak et al., *J. Gen. Virol.* 69:765 (1988)].

DNA encoding suitable signal sequences can be derived from genes for secreted insect or baculovirus proteins, such as the baculovirus polyhedrin gene [Carbonell et al., *Gene*, 73:409 (1988)]. Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon [Maeda et al., *Nature* 315:592 (1985)]; human gastrin-releasing peptide [Lebacq-Verheyden et al., *Molec. Cell. Biol.* 8:3129 (1988)]; human IL-2 (Smith et al., *Proc. Nat'l Acad. Sci. USA*, 82:8404 (1985)]; mouse IL-3 [Miyajima et al., *Gene*, 58:273 (1987); and human glucocerebrosidase [Martin et al., *DNA*, 7:99 (1988)] can also be used to provide for secretion in insects.

In some instances, as described above, it may be desirable to have a plurality of copies, two or more, of the gene expressing the expression product precursor in relation to the PACE DNA sequence or vice versa. Some of the embodiments of the present invention include recombinant production of multiple proteins, for instance PACE and one or several heterologous precursor polypeptides. This may be accomplished by several different strategies. For example, PACE may be produced by expression of a gene encoding PACE in the baculovirus/insect cell expression system described herein. PACE so produced may then be used to cleave enzymatically a heterologous precursor polypeptide, thereby generating a more mature form of the protein. Of course, both PACE and the precursor polypeptide may be produced by independent baculovirus/insect cell expression systems and subsequently admixed.

Alternatively, PACE and one or more precursor polypeptides may be simultaneously produced by expression of the corresponding genes in the same insect cell. Each gene may be introduced into the insect cell by a separate transformation event, for instance separate transfections, transfection and baculovirus infection, or multiple baculovirus infections. Various combinations will be apparent to those skilled in the art. Transfer vectors can also be constructed which have two or more sets of operably linked expression regulating elements described above. Each set of expression elements has a unique restriction site into which a different gene may be inserted. Each set of elements may use the same type of promoter, or a different promoter may be used for each set. The enzyme/substrate ratio of PACE and precursor polypeptides may be optimized by use of different promoters with varying relative efficiencies.

Finally, a transfer vector incorporating multiple genes encoding PACE and one or more precursor polypeptides may be designed such that all genes are expressed as a polycistronic message under the control of a single set of regulatory elements. The resulting polyprotein can be processed into component parts by the autocatalytic activity of the PACE moiety, or by the incorporation of recognition sites for a site specific endopeptidase, such as signal peptidase, between functional domains.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the heterologous protein from insect cells. The leader sequence fragment typically encodes a signal peptide comprised of hydrophobic amino acids which direct the translocation of the protein into the endoplasmic reticulum.

After insertion of the PACE DNA sequence and/or the gene encoding the expression product precursor, an insect cell host is co-transformed with the heterologous DNA of the transfer vector and the genomic DNA of wild type baculovirus—usually by co-transfection. The promoter and transcription termination sequence of the construct will typically comprise a 2–5 kb section of the baculovirus genome. Methods for introducing heterologous DNA into the desired site in the baculovirus virus are known in the art [see, e.g., Summers and Smith, cited above; Ju et al. (1987)

cited above; Smith et al., *Mol. Cell. Biol.*, 3:2156 (1983); and Luckow and Summers (1989) cited above]. For example, the insertion can be into a gene such as the polyhedrin gene, by homologous double crossover recombination; insertion can also be into a restriction enzyme site engineered into the desired baculovirus gene (Miller et al., *Bioessays*, 4:91 (1989)]. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. The beauty of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly retractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies ["Current Protocols in Microbiology", Vol. 2 (Ausubel et al. eds) at 16.8 (Supp. 10, 1990); Summers and Smith, cited above; Miller et al. (1989), cited above].

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda*, and *Trichoplusia ni* [P.C.T. Pub. No. WO89/046699; Carbonell et al., *J. Virol.* 56:153 (1985); Wright, *Nature* 321:718 (1986); Smith et al., *Mol. Cell. Biol.* 3:2156 (1983); and see generally, Fraser et al., *In Vitro Cell. Dev. Biol.* 25:225 (1989)].

Cells and cell culture media are commercially available for both direct and fusion expression of heterologous polypeptides in a baculovirus/expression system. Cell culture technology is generally known to those skilled in the art [see, e.g., Summers and Smith, cited above].

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by known techniques, such as, chromatography (e.g., HPLC, affinity chromatography, ion exchange chromatography), electrophoresis, density gradient centrifugation, solvent extraction, or the like. As appropriate, the product may be further purified, as required, to remove substantially any insect proteins which are also secreted in the medium or result from lysis of insect cells, to provide a product which is at least substantially free of host debris, e.g., proteins, lipids and polysaccharides.

D. Deposit of Biological Material

*Escherichia coli* strain HB101 host cells transformed with a plasmid containing the PACE gene of FIG. 2, PACE/pBS24.1 have been deposited on Nov. 30, 1990, with the American Type Culture Collection (ATCC), Rockville, Md., and designated as PACE/pBS24.1 in *E. coli*. This deposit will be maintained under the terms of the Budapest Treaty on the International Recognition of the Deposit of Microorganisms for purposes of patent procedure. The accession number is ATCC 68486.

This deposit is provided merely as convenience to those of skill in the art, and is not an admission that a deposit is required under 35 U.S.C. §112. The nucleic acid sequence [SEQ ID NO: 3] of this plasmid, as well as the amino acid sequence [SEQ ID NO: 4] of the polypeptide encoded thereby, are incorporated herein by reference and are controlling in the event of any conflict with the description herein. A license may be required to make, use, or sell the deposited material, and no such license is hereby granted.

The following experimental section is intended to be merely illustrative and does not limit the present scope in any way. The following examples illustratively describe the construction of plasmids for the expression and production of PACE in mammalian cells, and the co-expression of PACE and the blood coagulation factor, Factor IX, in mammalian cells.

EXAMPLE 1

Construction of PACE cDNA

This example demonstrates the construction of a composite recombinant cDNA which encodes mammalian PACE, and the characterization of the polypeptide encoded therein. The cDNA was constructed from two isolated cDNAs encoding separate portions of the PACE molecule.

The molecular cloning of cDNAs encoding PACE was accomplished as follows. An oriented cDNA library was constructed in the yeast expression vector pAB23BXN using poly(A)$^+$ mRNA isolated from the human liver cell line HEPG2. pAB23BXN is a derivative of pAB23BX [D. Schild et al., *Proc. Natl. Acad. Sci. U.S.A.*, 87:2916 (1990)] into which a synthetic polylinker, that contained Bst X1 and Not 1 sites, was inserted for unidirectional cDNA cloning. Oligonucleotide probes were used to isolate a 3,295 bp clone from the library. These probes were synthesized using the sequence of a partial cDNA clone (3.1 kb) which putatively encodes a portion of the fur gene product [A. J. M. Roebroek et al., *EMBO J.*, 5:2197 (1986)].

In order to isolate the 5'-end of the PACE cDNA, a second cDNA library from HEPG2 poly (A)$^+$ RNA mRNA was constructed in λZAPII [Stratagene], using specific internally primed message. Using the longest clone isolated from this library, a composite cDNA for PACE was constructed. The composite cDNA contains 4,351 bp and is comprised of 388 bp of 5'-untranslated region, a putative coding sequence corresponding to 794 amino acids, and 1597 bp of 3'-untranslated region, including two termination codons and a tail of 17 dA residues.

The full sequence of the composite PACE cDNA and the encoded protein sequence is shown in FIG. 2 [SEQ ID NO: 3] with the encoded protein sequence shown above that of the cDNA sequence. The numbering is based on the significant open reading frame (ORF) in the cDNA. Oligonucleotide adaptor sequences present in the cDNA are indicated by lower-case letters. The putative signal peptide is indicated by underlining and the transmembrane domain (TM) by shading. Likely active site residues are indicated by asterisks. Consensus sites for Asn-linked glycosylation are marked by diamonds and cysteine residues by bars. Potential dibasic proteolytic processing sites are indicated by arrows.

Based upon the composite PACE cDNA structure, the following is deduced. The translation of PACE is probably initiated at the ATG start codon at nucleotide #1. Although there are four ATG codons upstream from nucleotide #1, the ATG at nucleotide #1 is the only in-frame methionine codon in the 5'-region of the cDNA, and the subsequent 26 amino acids constitute a classical hydrophobic signal sequence, which is usually associated with a membrane-bound protein. The signal peptidase cleavage site occurs between amino acids #26–27.

A large ORF encodes a PACE precursor protein with a calculated molecular weight of 86.7 kD. In addition, several paired basic amino acid residues are located in the amino-terminal region of the PACE precursor (FIG. 2), and could represent proteolytic/autolytic processing sites. The coding sequence contains three consensus sites for N-linked glycosylation and twenty-two cysteine residues. The active site is in the ORF and includes a triad of amino acids: aspartic acid (Asp #153), histidine (His #194), and serine (Ser #368). A cysteine-rich region (CRR) is also present and, as shown in FIG. 2, is located in the vicinity of amino acid Cys #587 to amino acid Cys #675. A putative hydrophobic transmembrane domain (TM) is located downstream from the cysteine-rich region, at approximately amino acid Val #716 to amino acid Leu #738.

The 3'-untranslated region is relatively long (1597 bp) and contains a possible polyadenylation signal (ATTAAA) at nucleotides #3939–3943 of the composite clone. Of particular note are numerous regions of extensive potential secondary structure involving coding sequences, and the 3'-untranslated sequences around the termination codon.

EXAMPLE 2

Plasmid Construction and Expression of PACE cDNA in Mammalian COS-1 Cells

This example demonstrates the expression of recombinant PACE cDNA in COS-1 cells. The mammalian cell expression system was constructed as follows.

A truncated 2.47 kbp PACE cDNA fragment is employed, which was generated from the composite PACE cDNA by PCR. The method utilized synthetic primers which hybridized to the 5'-end of the PACE coding sequence and to approximately 70 bp into the 3'-untranslated region. The 5' primer generated an EcoRI site for cloning into pBluescript SK- [Stratagene]. The 3' primer generated a SalI cloning site. All of the PCR products were verified by the M13 dideoxy sequencing method.

The 2.47 kbp (EcoRI-SalI) PACE cDNA fragment from pBluescript-PACE included the 794 codon PACE coding sequence [SEQ ID NO: 1] (FIG. 1) and 74 bases of 3'-untranslated sequence before a SalI site [van den Ouweland et al, cited above]. At the 5'-end, using the EcoRI PCR primer, the sequence immediately preceding the ATG was modified to conform to the consensus translation start site.

The 2.47 kb truncated cDNA was inserted into the cloning site (EcoRI-SalI) of the SV40-based expression vector pMT3 to generate the plasmid pMT3-PACE. The pMT3 vector is a derivative of the vector pMT2 [R. J. Kaufman et al., Mol. Cell. Biol., 9:946 (1989)] in which the DHFR coding region on the 3'-side of the cloning site has been removed. pMT3 has been deposited with the American Type Culture Collection (ATCC), Rockville, Md. (USA) under Accession Number ATCC 40348. pMT3 can also be generated starting with pMT2-vWF, which is deposited at the ATCC under Accession Number ATCC #67122 [see PCT application PCT/US87/00033].

DNA of the resulting vector, pMT3-PACE, was purified and introduced for transient expression into SV40-transformed monkey kidney cells (COS-1) using a calcium phosphate transfection protocol as described in Chen, C. A., and Okayama, H., BioTechniques, 6:632–638 (1988); and C. Chen and H. Okayama, Mol. Cell. Biol. 7:745 (1987). Cells were transfected with 40 μg of plasmid per 10 cm dish in 10 mls of medium or, in the case of co-transfections, an equimolar ratio of plasmids totalling 60 μg per 10 cm dish in 10 ml of medium.

To monitor PACE synthesis, pMT3-PACE transfected COS-1 cells were radiolabeled 48–60 hours following transfection using S-labeled amino acids, e.g., $^{35}$S-Met and $^{35}$S-Cys, in medium lacking those amino acids, e.g., Cys and Met. Untransfected cells were similarly treated. After a 30 minute pulse period, cell extracts were prepared by lysis in NP-40 lysis buffer [A. J. Dorner and R. J. Kaufman (1990), Meth. Enzymol., 185:577 (1990)] or were chased by removing the labeling medium and replacing it with complete medium for additional incubation. Cell extracts and conditioned medium were treated with protease inhibitors and immunoprecipitated using the method described in Wise et al, Cell, 52:229–236 (1988).

Immunoprecipitates were performed with rabbit anti-PACE antiserum produced against a PACE-E. coli fusion protein. Rabbit anti-PACE antiserum was generated against the catalytic domain of PACE by expression of amino acids 146 to 372 of PACE as a human superoxide dismutase (SOD) fusion protein in E. coli. The DNA fragment for expression was generated by polymerase chain reaction (PCR) and cloned into the superoxide dismutase (SOD) fusion vector pTAC7 [Steimer et al, J. Virol., 58:9 (1986)]. The induced fusion protein was purified by preparative polyacrylamide gel electrophoresis, eluted and used to immunize rabbits in complete Freunds adjuvant.

The immunoprecipitated samples were then analyzed by SDS-polyacrylamide gel electrophoresis [SDS-PAGE; (A 8%; B,C 6% acrylamide)]. The gels were prepared for fluorography in EnHance [Dupont].

In the lysates from the control COS-1 cells which were not transfected with pMT3-PACE, immunoreactive proteins with anti-PACE antiserum were not detected. However, in extracts from pMT3-PACE transfected cells, immunoreactive species were detected that migrated in the gels primarily as a doublet of approximately 90 kD. These PACE immunoprecipitates were treated with the endoglycosidase enzyme, N-glycanase [Genzyme], using the method described in A. J. Dorner and R. J. Kaufman (1990), cited above. This treatment resulted in a shift in the electrophoretic mobility of the labeled proteins in the gels which was consistent with the presence of asparagine-linked oligosaccharides. However, these digestions did not fully reduce the complexity of the bands, suggesting that differential glycosylation may not be the source of the observed heterogeneity in the expressed PACE.

In order to analyze secretion of PACE, the $^{35}$S-labeled cells were incubated for a 12 hour chase period in a medium containing an excess of unlabeled amino acids. The secreted products from the conditioned medium and in cell lysates were immunoprecipitated with the anti-PACE antiserum. The medium from the pMT3-PACE transfected cells yielded an immunoreactive protein which migrated in the gels as a 75 kD polypeptide. The relative quantity of the 75 kD immunoprecipitated PACE polypeptide observed in the conditioned medium was 5 to 10 fold less than that detected in the cell lysate or remaining inside the cell at the 12 hour chase period.

This secreted PACE species, which differs in apparent size from the intracellular species, may represent a truncated molecule which is missing its transmembrane and/or intracellular domains. This difference in size may possibly be the result of auto-proteolysis at the paired arginine residues, #497-498, due to the large overproduction of PACE in the transfected COS-1 cells.

More extensive pulse-chase experiments demonstrated that the PACE translation product does not accumulate to high levels inside the cell compared to another integral membrane glycoprotein (influenza hemagglutinin) when synthesized at similar levels.

EXAMPLE 3

Coexpression of PACE and vWF in Cos-1 Cells

This example demonstrates the effect of recombinant PACE expression on the processing of von Willebrand factor (vWF), a protein involved in blood coagulation, produced during co-expression of the two recombinant polypeptides in COS-1 cells.

vWF is a multimeric plasma protein which is normally synthesized in endothelial cells as a large precursor polypeptide (prepro-vWF). Upon translocation into the endoplasmic reticulum (ER), the precursor polypeptide undergoes signal peptide cleavage and N-linked oligosaccharide addition. In the ER, pro-vWF forms carboxy-terminal linked disulfide-bonded dimers that, upon transport to the Golgi and post-Golgi compartments, undergo a complex series of processing steps. These steps include: processing of N-linked carbohydrate, O-linked glycosylation, assembly of disulfide linked multimers, and propeptide cleavage [R. I. Handin and D. D. Wagner, in *Proaress in Hemostasis and Thrombosis*, vol 9, B. S. Coller, Ed. (W. B. Saunders, Philadelphia, 1989) pp. 233–259].

In endothelial cells, vWF follows both a constitutive and regulated pathway of secretion. Transfection of a vWF cDNA expression vector into COS-1 cells directs the synthesis of prepro-vWF [D. T. Bonthron et al., *Nature*, 324:270 (1986)]. However, although COS-1 cells do possess a protease capable of recognizing and cleaving the vWF propeptide, this process is inefficient. Thus, approximately 50% of the secreted protein from a typical expression study is uncleaved pro-vWF [R. J. Wise et al., *Cell*, 52:229 (1988)]. If PACE recognizes and cleaves the vWF propeptide, then co-expression of PACE with Pro-vWF should result in greater conversion of pro-vWF to the mature form.

In order to demonstrate PACE conversion of pro-vWF to the mature form, COS-1 cells were transfected with either pMT3-PACE, pMT2-vWF [D. T. Bonrthron et al., *Nature*, 324:270 (1986)], or cotransfected with both plasmids. Cells were transfected with 40 μg of plasmid, or in the case of co-transfections with an equimolar ratio of plasmids totaling 60 μg per 10 cm dish in 10 ml of medium. The transfected cells were pulse-labeled with $^{35}$S-amino acids for 30 minutes and lysed, as described in Example 2, or were chased by removing the labeling medium and replacing it with complete medium for additional incubation.

Cell extracts and conditioned medium samples were treated with protease inhibitors and immuno-precipitated. Immunoprecipitation was with an anti-vWF polyclonal antibody [Dako Corp.] which specifically recognizes the mature portion of vWF. The same samples were also immunoprecipitated with a monoclonal antibody specific for the propeptide of vWF (anti-vWAgII).

Immunoprecipitation of cell extracts from 30 minute pulse-labeled cells with anti-VWF antibody detected only single chain pro-vWF precursor in COS-1 cells transfected with pMT2-vWF alone. The conditioned medium yielded both cleaved (mature) and uncleaved (pro-vWF) forms in nearly equal amounts.

In contrast, in cellular extracts of COS-1 cells that were co-transfected with pMT2-vWF and pMT3-PACE, the 100 kD propeptide and 225 kD mature subunit were detected at the 30 minute pulse time point. This indicates that there was a significant amount of propeptide cleavage at this time point. In the conditioned medium, following a 12 hour chase period, the secreted vWF was completely processed to the 225 kD mature protein. Analysis of the amino-terminus of $^{35}$S-Met labeled 225 kD product by 21 cycles of automated Edman degradation, followed by scintillation counting, yielded results which were consistent with cleavage at the correct site within the-vWF precursor.

Cleavage of pro-vWF to the mature form of vWF also yields the vWF propeptide. The production of this propeptide in the above studies was also monitored. The presence of this propeptide was shown by immunoprecipitation with a monoclonal antibody directed against the propeptide, also known as vWF Antigen II [P. J. Fay et al., *Nature*, 232:995 (1986)]. Analysis of the immunoprecipitated products was by polyacrylamide gel electrophoresis, as described above.

The results showed that immunoprecipitates from extracts of cells transfected with pMT2-vWF alone yielded unprocessed pro-vWF (due to the presence of the uncleaved propeptide in the precursor molecule). Immunoprecipitates of extracts from cells co-transfected with pMT2-vWF and pMT3-PACE yielded the vWF propeptide, which migrated in the gels as a doublet at 100 kD. The doublet was reduced to a single species after digestion with N-glycanase, indicating that the apparent difference in molecular weights was due to differential glycosylation.

Using a similar analysis, the conditioned cell media were also analyzed for the presence of propeptide. Immunoprecipitates of the conditioned medium of the pMT2-vWF transfected cells yielded the free propeptide and multimers of vWF. The multimers contained a mixture of mature vWF and pro-vWF, indicating incomplete processing in the singly transfected COS-1 cells. However, the anti-AgII antibody immuno-precipitates from the conditioned medium from co-transfected cells yielded only free propeptide, indicating that the pro-vWF had been totally converted into the mature form.

In these studies with the detection of the propeptide, formation of vWF multimers in the media from singly transfected and co-transfected cells was confirmed by non-reducing agarose gel electrophoresis, using essentially the technique described by R. J. Wise et al., *Cell*, 52:229 (1988). The agarose gel electrophoresis analysis indicated that the amount of vWF multimers in the media from the singly and co-transformed cells was comparable.

EXAMPLE 4

Substrate Specificity of PACE

In order to test the recognition specificity of the recombinant PACE for substrates with a Lys-Arg or Lys-Lys cleavage site, studies were performed with mutants in the cleavage site of pro-vWF. One of the mutants, designated vWF DES, contained a non-conservative substitution, Lys-Arg-Ser (KRS) to Asp-Glu-Ser (DES), at the propeptide cleavage site. The other mutant, designated vWF KKS, contained a conservative substitution of Lys-Lys-Ser for Lys-Arg-Ser at the propeptide cleavage site.

Plasmids containing the mutant vWF genes were co-transfected with pMT3-PACE to determine the susceptibility of their expression products to cleavage with PACE. The analysis was carried out as described in Example 3 above.

The results of the analysis showed that when COS-1 cells were transfected with the plasmid encoding vWF DES, the labeled product was secreted as an uncleaved pro-vWF species. The same results were obtained with COS-1 cells which were co-transformed with both the vWF DES plasmid and with pMT3-PACE. When the expression products of COS-1 cells transfected with the plasmid encoding vWF KKS were examined, the labeled product was again secreted as an uncleaved pro-vWF species. When the expression products of the co-transformants which expressed both PACE and the KKS mutant protein were examined, although some of the secreted vWF remained uncleaved, a significant amount of propeptide cleavage had occurred.

The results of these studies with the mutated vWF sequences indicates that a non-conservative substitution at the natural Lys-Arg cleavage site of pro-vWF prevents cleavage by co-expressed recombinant PACE. However, a conservative substitution of Lys-Lys for Lys-Arg still allows an acceptable substrate for the recombinant protease.

EXAMPLE 5

Expression of PACE in CHO Cells

This example illustrates the transformation of Chinese hamster ovary (CHO) cells with the PACE coding sequence. Suitable vectors were constructed as follows. pMT3-PACE was digested with SalI to linearize at the 3' end of PACE cDNA. The SalI site was filled-in with dNTPs and Klenow. The EcoRI linker was ligated to a blunt end and then digested with EcoRI. PACE cDNA was isolated on a gel and then ligated to EcoRI-linearized pMT2-EMC-DHFR. This latter plasmid is a minor derivative of pED4, described in R. Kaufman et al, *Nucl. Acids Res.,* 19(16):4485–4490 (1991).

Transformed DH5α colonies were picked for plasmid miniprep. Insert orientation was determined with KpnI, BamHI, Bgl1I. The properly oriented clone was grown for large-scale plasmid preparation. The remainder of the miniprep DNA was used to transfect two CHO cell lines.

A lipofection kit [BRL] was used to transfect CHO cells on 60 mm culture dishes in OptiMEM medium. The two starting cell lines were CHO-DUKX and PM5F-0.1, which is a VWF-producing line derived from PM5F by selection for resistance of 0.1 μM DCF.

α-selection was started after splitting the cells to 100 mm plates. The CHO-DUKX line was selected in α-MEM/10% dialysed fetal calf serum (FCS). The PM5F line was selected in α-MEM-AAU/10% dialysed FCS. Both lines showed good growth during 3 days of a α-medium selection. These α-selected cells were split. One plate of each line (called PACE-DUKX-α and PM5F-PACE-α) was passaged in α-medium for 10 days then frozen for storage.

Methotrexate (MTX) was added (0.05 μM) to the selection medium four days later. Many colonies formed over approximately 1 week. These colonies were pooled and split for selection in methotrexate at 0.1 μM about a week later. Again, many colonies formed which were pooled, split and continued in selection medium with 0.1 μM methotrexate. These amplified pools were then frozen for storage.

PM5F-PACE ("pool A") cells were pulse-labeled. Two subconfluent 100 mm plates were rinsed in serum-free medium. 1 ml of Cys/Met deficient medium supplemented with 250 μCi each of 35-S Met and 35-S Cys was added for a 15 minute pulse. One plate was lysed for immunoprecipitation of cell extract. Medium was removed from the other plate and 2 ml complete medium (serum-free) added for a 12 hour chase. At 12 hours, conditioned medium was collected and cells were lysed for immunoprecipitation. Cell lysis was in 1 ml of cold 0.5% Triton-X-100, M NaCl, 10 Mm Tris-HCl (pH 7.5), 5 Mm Na2-EDTA. Protease inhibitors were added to conditioned medium and cell extract. Immunoprecipitates of 0.5 ml of cell extract and 1 ml conditioned medium were performed with an anti-vWF antibody [DAKO] coupled two Affi-Gel and an anti-PACE antiserum [Chiron] secondarily bound to protein-A sepharose.

Precipitates were washed in cold lysis buffer and analysed on SDS-PAGE. Results were similar to that seen in PACE plus vWF COS-1 co-transfection experiments. With anti-PACE, a 95–100 kDA doublet band was precipitated in the 15 minute cell extract. At 12 hours, the intensity of this cell extract band was reduced approximately 10 fold. In the conditioned medium, at 12 hours, a 75–80 kDa single band was detected. With the anti-vWF, it was determined that the secreted vWF at 12 hours was completely processed mature vWF. In the cell extract samples, both pro-vWF and cleaved vWF were present.

These findings differ from that observed in the parent cell line, PM5F, in that secreted vWF is only partially processed and intracellular cleavage is minimal. For PM5F-PACE, a comparison of the autoradiographic intensities of the PACE bands and the vWF bands indicated that the level PACE expression is roughly ½ that of vWF.

The PACE-DUKX ("pool 4/4") was tested in the manner described above. The SDS-PAGE results from anti-PACE immunoprecipitates demonstrated an intracellular 95–100 kDa doublet band in pulsed (30 minute) cell extract and the apparent secretion of a smaller (75–80 kDa) immunoreactive species in the chased (18 hour) conditioned medium. In addition, in this labeling experiment, PM5F-PACE cells were analyzed for comparison. The intensities of the PACE bands in the 30 minute cell extract immunoprecipitates were equal for both cell lines.

EXAMPLE 6

Co-Expression of PACE and Factor IX in CHO Cells

A CHO cell line producing recombinant Factor IX (IC4) [the IC4 cell line is described in Kaufman et al, *J. Biol. Chem.*, 261:9622–9628 (1986)] and Factor IX sequences were transfected with the PACE cDNA described above in Example 1 operably linked to another amplifiable marker, adenosine deaminase. The vector MT3SV2Ada [R. J. Kaufman et al, *Meth. Enzym.*, 185:537–566 (1990)] was chosen for PACE expression because it contains a selectable ADA transcription unit but no DHFR sequences and the PACE fragment could easily be inserted after digestion of the vector with EcoR1 and Sal1.

A vector fragment was isolated from low melt agarose, ligated in a ratio of 5:1 (fragment to vector), diluted in 10 mM Tris-HCl, pH 7.5, 1 mM EDTA, and used to transform DH5 bacteria [Dr. Douglas Hanahan, Cold Spring Harbor, N.Y.]. A nick-translated, $^{32}$p labelled PACE fragment was prepared and used for filter hybridization to screen transformed colonies.

Positively hybridizing colonies were isolated and DNA prepared for digestion with EcoRl and SalI for confirmation of PACE insertion and with Bgl II for correct orientation of the fragment with respect to adenovirus major late promoter in the vector.

DNA from one colony was isolated for electroporation into the Factor IX producing cells, IC4. Pools of colonies have been selected for amplification by growth in 1.0 μM 2'-deoxycoformycin (DCF). The presence of PACE in these amplified lines was confirmed by $^{35}$S-methionine labelling and immunoprecipitation.

Biological activity of the Factor IX protein in the PACE/IX pools was analyzed by clotting assay, performed as described in Kaufman et al, *J. Biol. Chem.*, 261:9622–9628 (1986). Cells were plated in p60 tissue culture dishes. The next day medium was reduced (1.5 ml) and changed to α "defined"+1 μg/ml Vitamin K3.

The PACE/Factor IX pools were found to secrete between 2.0 and 3.1 fold more Factor IX biological activity than the original IC4 cell line. The results of a radioimmunoassay indicated increased levels of γ-carboxylated protein. These results are illustrated in Table I below.

The coexpression of PACE did not produce any detectable change in the size of the Factor IX protein as monitored by immunoprecipitation with a FIX antibody [Hybridtech] and SDS gel electrophoresis.

EXAMPLE 7

Baculovirus Expression of PACE

Two baculovirus expression cassettes were constructed for expression of PACE in insect cells. Cassette I was constructed using as the PCR template, PACE/pBS24.1, with primers fur 102 and fur 103:

102: 5'CCA CCT GTC TGA TCA ATG GAG CTG AGG CCC TGG TTG3' [SEQ ID NO: 5]
103: 5'GAG GCC TGA TCA CTA CTC AGC CAG GTG TGA GGG CAT3' [SEQ ID NO: 6].

The cassette was made without a transmembrane domain. The pCR product was extracted with phenol/chloroform and precipitated with ethanol. The PCR product was then cut with BclI and ligated to the pAC373 vector, which was cut

TABLE I

Factor IX Assays in Original IC4 and PACE Co-expressing Cell Lines

| | | | | | | RIA | |
| --- | --- | --- | --- | --- | --- | --- | --- |
| Cell | CLOTTING ASSAY U/ml (pg/cell) | | CLOTTING ASSAY U/ml (pg/cell) | | GLA μg/mL | TOTAL μg/mL (pg/cell) | GLA TOTAL |
| IC4 | .28 | (.32) | .18 | (.18) | .1 | 20 (30) | .5% |
| Co-expressors | 0.1 μM DCF | | 1.0 μM DCF | | | 5 μM DCF | |
| A | .72 | (.89) 2.7x | .45 | (.48) 2.6x | .69 | 20 (29) | 3.4% |
| B | .53 | (.76) 2.3x | .39 | (.41) 2.3x | 1.05 | 22 (27) | 4.8% |
| C | .66 | (.73) 2.2x | .35 | (.41) 2.3x | .17 | 19 (54) | .8% |
| D | .46 | (.66) 2.0x | .55 | (.55) 3.1x | 1.14 | 17 (24) | 6.7% |
| E | .67 | (.80) 2.5x | .49 | (.52) 2.9x | .3 | 11 (34) | 2.7% |

From the first electroporation of MT3-PACE Ada into IC4 cells, cells were selected in α medium with 10% dialyzed fetal calf serum, penicillin, streptomycin, glutamine, 200 μM Methotrexate and Adenosine, alanosine, uridine and 0.1 μM DCF. Approximately 25 colonies were observed in plates that did not receive DNA.

A second electroporation performed was selected in the same manner and approximately 100 colonies were pooled into each of the 5 pools. No colonies were observed on plates that did not receive DNA.

Expression of PACE was detected in each pool by 30 minute pulse with $^{35}$S Methionine followed by 2 hour chase and immunoprecipitation of cell extracts with α PACE antibody [Chiron Corporation, California]. In cells which express higher levels of PACE as a result of selection for further DCF resistance, secretion up to 10-fold greater levels of μ-carboxylated Factor IX was observed compared to the original IC4 cell line.

with Bam HI and phosphatased. Cassette II was constructed using as the PCR template, PACE/pBS24.1, with primers fur 102 (above) and fur 104:

104: 5'GCA GCC TGA TCA CTA TGG AGG TAC GGG CAG CCC CTC3' [SEQ ID NO: 7].

The pCR product was purified and cloned into pAC373 by the procedure described above for Construct I.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A cDNA sequence encoding a soluble mammalian endopeptidase protein precursor processing enzyme, PACE, capable of cleaving precursor polypeptides which require gamma-carboxylation for biological activity at basic amino acid pairs, said cDNA sequence encoding the PACE polypeptide encoded by SEQ ID NO: 1 or SEQ ID NO: 3 truncated at between about nucleotide number 2553 and about nucleotide number 2621.

2. A recombinant expression vector suitable for expression in a selected host cell comprising a cDNA sequence encoding a soluble mammalian endopeptidase protein precursor processing enzyme, PACE, having a biological activity of cleaving precursor polypeptides which require gamma-carboxylation for biological activity at basic amino acid pairs, and wherein said cDNA sequence is SEQ ID NO: 1 or SEQ D NO: 3 truncated between nucleotide number 2553 and nucleotide number 2621.

3. The vector according to claim 2, wherein the encoded PACE retains PACE biological activity and is a soluble truncation of SEQ ID NO:2.

4. A transformed host cell comprising a recombinant cDNA sequence heterologous to said host cell and encoding a soluble mammalian endopeptidase protein precursor processing enzyme, PACE, having a biological activity of cleaving precursor polypeptides which require gamma-carboxylatioin for biological activity at basic amino acid pairs, wherein said PACE encoding sequence is operably linked to an expression control sequence permitting expression of PACE by said cell, and wherein said cDNA sequence is SEQ ID NO: 1 or SEQ ID NO: 3 truncated between nucleotide number 2553 and nucleotide number 2621.

5. The host cell according to claim 4 wherein said expression control sequence is heterologous to said host cell.

6. The host cell according to claim 4, which is a bacterial cell.

7. The host cell according to claim 4, wherein said encoded PACE retains PACE biological activity and is a soluble truncation of SEQ ID NO:2.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 2385 base pairs
      (B) TYPE: nucleic acid
      (C) STRANDEDNESS: double
      (D) TOPOLOGY: unknown (ii) MOLECULE TYPE: DNA (genomic)

(ix) FEATURE:
      (A) NAME/KEY: CDS
      (B) LOCATION: 1..2382

(x) PUBLICATION INFORMATION:
      (A) AUTHORS: van den Ouweland W., A. M.
      (C) JOURNAL: Nucleic Acids Res.
      (D) VOLUME: 18
      (F) PAGES: 664-
      (G) DATE: 1990

(xi) SEQUENCE DESCRIPTION: SEQ ID NO:1:

```
ATG GAG CTG AGG CCC TGG TTG CTA TGG GTG GTA GCA GCA ACA GGA ACC      48
Met Glu Leu Arg Pro Trp Leu Leu Trp Val Val Ala Ala Thr Gly Thr
 1               5                  10                  15

TTG GTC CTG CTA GCA GCT GAT GCT CAG GGC CAG AAG GTC TTC ACC AAC      96
Leu Val Leu Leu Ala Ala Asp Ala Gln Gly Gln Lys Val Phe Thr Asn
             20                  25                  30

ACG TGG GCT GTG CGC ATC CCT GGA GGC CCA GCG GTG GCC AAC AGT GTG     144
Thr Trp Ala Val Arg Ile Pro Gly Gly Pro Ala Val Ala Asn Ser Val
         35                  40                  45

GCA CGG AAG CAT GGG TTC CTC AAC CTG GGC CAG ATC TTC GGG GAC TAT     192
Ala Arg Lys His Gly Phe Leu Asn Leu Gly Gln Ile Phe Gly Asp Tyr
     50                  55                  60

TAC CAC TTC TGG CAT CGA GGA GTG ACG AAG CGG TCC CTG TCG CCT CAC     240
Tyr His Phe Trp His Arg Gly Val Thr Lys Arg Ser Leu Ser Pro His
 65                  70                  75                  80

CGC CCG CGG CAC AGC CGG CTG CAG AGG GAG CCT CAA GTA CAG TGG CTG     288
Arg Pro Arg His Ser Arg Leu Gln Arg Glu Pro Gln Val Gln Trp Leu
                 85                  90                  95

GAA CAG CAG GTG GCA AAG CGA CGG ACT AAA CGG GAC GTG TAC CAG GAG     336
Glu Gln Gln Val Ala Lys Arg Arg Thr Lys Arg Asp Val Tyr Gln Glu
            100                 105                 110

CCC ACA GAC CCC AAG TTT CCT CAG CAG TGG TAC CTG TCT GGT GTC ACT     384
Pro Thr Asp Pro Lys Phe Pro Gln Gln Trp Tyr Leu Ser Gly Val Thr
        115                 120                 125

CAG CGG GAC CTG AAT GTG AAG GCG GCC TGG GCG CAG GGC TAC ACA GGG     432
Gln Arg Asp Leu Asn Val Lys Ala Ala Trp Ala Gln Gly Tyr Thr Gly
    130                 135                 140

CAC GGC ATT GTG GTC TCC ATT CTG GAC GAT GGC ATC GAG AAG AAC CAC     480
His Gly Ile Val Val Ser Ile Leu Asp Asp Gly Ile Glu Lys Asn His
145                 150                 155                 160

CCG GAC TTG GCA GGC AAT TAT GAT CCT GGG GCC AGT TTT GAT GTC AAT     528
Pro Asp Leu Ala Gly Asn Tyr Asp Pro Gly Ala Ser Phe Asp Val Asn
                165                 170                 175

GAC CAG GAC CCT GAC CCC CAG CCT CGG TAC ACA CAG ATG AAT GAC AAC     576
Asp Gln Asp Pro Asp Pro Gln Pro Arg Tyr Thr Gln Met Asn Asp Asn
            180                 185                 190

AGG CAC GGC ACA CGG TGT GCG GGG GAA GTG GCT GCG GTG GCC AAC AAC     624
```

```
          Arg His Gly Thr Arg Cys Ala Gly Glu Val Ala Ala Val Ala Asn Asn
                      195                 200                 205

GGT GTC TGT GGT GTA GGT GTG GCC TAC AAC GCC CGC ATT GGA GGG GTG          672
Gly Val Cys Gly Val Gly Val Ala Tyr Asn Ala Arg Ile Gly Gly Val
210                 215                 220

CGC ATG CTG GAT GGC GAG GTG ACA GAT GCA GTG GAG GCA CGC TCG CTG          720
Arg Met Leu Asp Gly Glu Val Thr Asp Ala Val Glu Ala Arg Ser Leu
225                 230                 235                 240

GGC CTG AAC CCC AAC CAC ATC CAC ATC TAC AGT GCC AGC TGG GGC CCC          768
Gly Leu Asn Pro Asn His Ile His Ile Tyr Ser Ala Ser Trp Gly Pro
                245                 250                 255

GAG GAT GAC GGC AAG ACA GTG GAT GGG CCA GCC CGC CTC GCC GAG GAG          816
Glu Asp Asp Gly Lys Thr Val Asp Gly Pro Ala Arg Leu Ala Glu Glu
            260                 265                 270

GCC TTC TTC CGT GGG GTT AGC CAG GGC CGA GGG GGG CTG GGC TCC ATC          864
Ala Phe Phe Arg Gly Val Ser Gln Gly Arg Gly Gly Leu Gly Ser Ile
        275                 280                 285

TTT GTC TGG GCC TCG GGG AAC GGG GGC CGG GAA CAT GAC AGC TGC AAC          912
Phe Val Trp Ala Ser Gly Asn Gly Gly Arg Glu His Asp Ser Cys Asn
290                 295                 300

TGC GAC GGC TAC ACC AAC AGT ATC TAC ACG CTG TCC ATC AGC AGC GCC          960
Cys Asp Gly Tyr Thr Asn Ser Ile Tyr Thr Leu Ser Ile Ser Ser Ala
305                 310                 315                 320

ACG CAG TTT GGC AAC GTG CCG TGG TAC AGC GAG GCC TGC TCG TCC ACA         1008
Thr Gln Phe Gly Asn Val Pro Trp Tyr Ser Glu Ala Cys Ser Ser Thr
                325                 330                 335

CTG GCC ACG ACC TAC AGC AGT GGC AAC CAG AAT GAG AAG CAG ATC GTG         1056
Leu Ala Thr Thr Tyr Ser Ser Gly Asn Gln Asn Glu Lys Gln Ile Val
            340                 345                 350

ACG ACT GAC TTG CGG CAG AAG TGC ACG GAG TCT CAC ACG GGC ACC TCA         1104
Thr Thr Asp Leu Arg Gln Lys Cys Thr Glu Ser His Thr Gly Thr Ser
        355                 360                 365

GCC TCT GCC CCC TTA GCA GCC GGC ATC ATT GCT CTC ACC CTG GAG GCC         1152
Ala Ser Ala Pro Leu Ala Ala Gly Ile Ile Ala Leu Thr Leu Glu Ala
370                 375                 380

AAT AAG AAC CTC ACA TGG CGG GAC ATG CAA CAC CTG GTG GTA CAG ACC         1200
Asn Lys Asn Leu Thr Trp Arg Asp Met Gln His Leu Val Val Gln Thr
385                 390                 395                 400

TCG AAG CCA GCC CAC CTC AAT GCC AAC GAC TGG GCC ACC AAT GGT GTG         1248
Ser Lys Pro Ala His Leu Asn Ala Asn Asp Trp Ala Thr Asn Gly Val
                405                 410                 415

GGG CGG AAA GTG AGC CAC TCA TAT GGC TAC GGG CTT TTG GAC GCA GGC         1296
Gly Arg Lys Val Ser His Ser Tyr Gly Tyr Gly Leu Leu Asp Ala Gly
            420                 425                 430

GCC ATG GTG GCC CTG GCC CAG AAT TGG ACC ACA GTG GCC CCC CAG CGG         1344
Ala Met Val Ala Leu Ala Gln Asn Trp Thr Thr Val Ala Pro Gln Arg
        435                 440                 445

AAG TGC ATC ATC GAC ATC CTC ACC GAG CCC AAA GAC ATC GGG AAA CGG         1392
Lys Cys Ile Ile Asp Ile Leu Thr Glu Pro Lys Asp Ile Gly Lys Arg
450                 455                 460

CTC GAG GTG CGG AAG ACC GTG ACC GCG TGC CTG GGC GAG CCC AAC CAC         1440
Leu Glu Val Arg Lys Thr Val Thr Ala Cys Leu Gly Glu Pro Asn His
465                 470                 475                 480

ATC ACT CGG CTG GAG CAC GCT CAG GCG CGG CTC ACC CTG TCC TAT AAT         1488
Ile Thr Arg Leu Glu His Ala Gln Ala Arg Leu Thr Leu Ser Tyr Asn
                485                 490                 495

CGC CGT GGC GAC CTG GCC ATC CAC CTG GTC AGC CCC ATG GGC ACC CGC         1536
Arg Arg Gly Asp Leu Ala Ile His Leu Val Ser Pro Met Gly Thr Arg
            500                 505                 510

TCC ACC CTG CTG GCA GCC AGG CCA CAT GAC TAC TCC GCA GAT GGG TTT         1584
```

```
Ser Thr Leu Leu Ala Ala Arg Pro His Asp Tyr Ser Ala Asp Gly Phe
    515                 520                 525

AAT GAC TGG GCC TTC ATG ACA ACT CAT TCC TGG GAT GAG GAT CCC TCT      1632
Asn Asp Trp Ala Phe Met Thr Thr His Ser Trp Asp Glu Asp Pro Ser
530                 535                 540

GGC GAG TGG GTC CTA GAG ATT GAA AAC ACC AGC GAA GCC AAC AAC TAT      1680
Gly Glu Trp Val Leu Glu Ile Glu Asn Thr Ser Glu Ala Asn Asn Tyr
545                 550                 555                 560

GGG ACG CTG ACC AAG TTC ACC CTC GTA CTC TAT GGC ACC GCC CCT GAG      1728
Gly Thr Leu Thr Lys Phe Thr Leu Val Leu Tyr Gly Thr Ala Pro Glu
                565                 570                 575

GGG CTG CCC GTA CCT CCA GAA AGC AGT GGC TGC AAG ACC CTC ACG TCC      1776
Gly Leu Pro Val Pro Pro Glu Ser Ser Gly Cys Lys Thr Leu Thr Ser
            580                 585                 590

AGT CAG GCC TGT GTG GTG TGC GAG GAA GGC TTC TCC CTG CAC CAG AAG      1824
Ser Gln Ala Cys Val Val Cys Glu Glu Gly Phe Ser Leu His Gln Lys
        595                 600                 605

AGC TGT GTC CAG CAC TGC CCT CCA GGC TTC GCC CCC CAA GTC CTC GAT      1872
Ser Cys Val Gln His Cys Pro Pro Gly Phe Ala Pro Gln Val Leu Asp
    610                 615                 620

ACG CAC TAT AGC ACC GAG AAT GAC GTG GAG ACC ATC CGG GCC AGC GTC      1920
Thr His Tyr Ser Thr Glu Asn Asp Val Glu Thr Ile Arg Ala Ser Val
625                 630                 635                 640

TGC GCC CCC TGC CAC GCC TCA TGT GCC ACA TGC CAG GGG CCG GCC CTG      1968
Cys Ala Pro Cys His Ala Ser Cys Ala Thr Cys Gln Gly Pro Ala Leu
                645                 650                 655

ACA GAC TGC CTC AGC TGC CCC AGC CAC GCC TCC TTG GAC CCT GTG GAG      2016
Thr Asp Cys Leu Ser Cys Pro Ser His Ala Ser Leu Asp Pro Val Glu
            660                 665                 670

CAG ACT TGC TCC CGG CAA AGC CAG AGC AGC CGA GAG TCC CCG CCA CAG      2064
Gln Thr Cys Ser Arg Gln Ser Gln Ser Ser Arg Glu Ser Pro Pro Gln
        675                 680                 685

CAG CAG CCA CCT CGG CTG CCC CCG GAG GTG GAG GCG GGG CAA CGG CTG      2112
Gln Gln Pro Pro Arg Leu Pro Pro Glu Val Glu Ala Gly Gln Arg Leu
    690                 695                 700

CGG GCA GGG CTG CTG CCC TCA CAC CTG CCT GAG GTG GTG GCC GGC CTC      2160
Arg Ala Gly Leu Leu Pro Ser His Leu Pro Glu Val Val Ala Gly Leu
705                 710                 715                 720

AGC TGC GCC TTC ATC GTG CTG GTC TTC GTC ACT GTC TTC CTG GTC CTG      2208
Ser Cys Ala Phe Ile Val Leu Val Phe Val Thr Val Phe Leu Val Leu
                725                 730                 735

CAG CTG CGC TCT GGC TTT AGT TTT CGG GGG GTG AAG GTG TAC ACC ATG      2256
Gln Leu Arg Ser Gly Phe Ser Phe Arg Gly Val Lys Val Tyr Thr Met
            740                 745                 750

GAC CGT GGC CTC ATC TCC TAC AAG GGG CTG CCC CCT GAA GCC TGG CAG      2304
Asp Arg Gly Leu Ile Ser Tyr Lys Gly Leu Pro Pro Glu Ala Trp Gln
        755                 760                 765

GAG GAG TGC CCG TCT GAC TCA GAA GAG GAC GAG GGC CGG GGC GAG AGG      2352
Glu Glu Cys Pro Ser Asp Ser Glu Glu Asp Glu Gly Arg Gly Glu Arg
    770                 775                 780

ACC GCC TTT ATC AAA GAC CAG AGC GCC CTC TGA                          2385
Thr Ala Phe Ile Lys Asp Gln Ser Ala Leu
785                 790
```

(2) INFORMATION FOR SEQ ID NO:2:

(i) SEQUENCE CHARACTERISTICS:
        (A) LENGTH: 794 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Leu Arg Pro Trp Leu Trp Val Val Ala Ala Thr Gly Thr
 1               5                  10                  15

Leu Val Leu Ala Ala Asp Ala Gln Gly Gln Lys Val Phe Thr Asn
                20                  25                  30

Thr Trp Ala Val Arg Ile Pro Gly Pro Ala Val Ala Asn Ser Val
            35                  40                  45

Ala Arg Lys His Gly Phe Leu Asn Leu Gly Gln Ile Phe Gly Asp Tyr
        50                  55                  60

Tyr His Phe Trp His Arg Gly Val Thr Lys Arg Ser Leu Ser Pro His
 65                  70                  75                  80

Arg Pro Arg His Ser Arg Leu Gln Arg Glu Pro Gln Val Gln Trp Leu
                    85                  90                  95

Glu Gln Gln Val Ala Lys Arg Thr Lys Arg Asp Val Tyr Gln Glu
                100                 105                 110

Pro Thr Asp Pro Lys Phe Pro Gln Gln Trp Tyr Leu Ser Gly Val Thr
            115                 120                 125

Gln Arg Asp Leu Asn Val Lys Ala Ala Trp Ala Gln Gly Tyr Thr Gly
        130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
                180                 185                 190

Arg His Gly Thr Arg Cys Ala Gly Glu Val Ala Ala Val Ala Asn Asn
                195                 200                 205

Gly Val Cys Gly Val Gly Val Ala Tyr Asn Ala Arg Ile Gly Gly Val
210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
                260                 265                 270

Ala Phe Phe Arg Gly Val Ser Gln Gly Arg Gly Gly Leu Gly Ser Ile
            275                 280                 285

Phe Val Trp Ala Ser Gly Asn Gly Gly Arg Glu His Asp Ser Cys Asn
290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
        370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415
```

Gly Arg Lys Val Ser His Ser Tyr Gly Tyr Gly Leu Leu Asp Ala Gly
                420                 425                 430

Ala Met Val Ala Leu Ala Gln Asn Trp Thr Thr Val Ala Pro Gln Arg
                435                 440                 445

Lys Cys Ile Ile Asp Ile Leu Thr Glu Pro Lys Asp Ile Gly Lys Arg
                450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
                500                 505                 510

Ser Thr Leu Leu Ala Ala Arg Pro His Asp Tyr Ser Ala Asp Gly Phe
                515                 520                 525

Asn Asp Trp Ala Phe Met Thr Thr His Ser Trp Asp Glu Asp Pro Ser
                530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
                580                 585                 590

Ser Gln Ala Cys Val Val Cys Glu Glu Gly Phe Ser Leu His Gln Lys
                595                 600                 605

Ser Cys Val Gln His Cys Pro Pro Gly Phe Ala Pro Gln Val Leu Asp
                610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
                660                 665                 670

Gln Thr Cys Ser Arg Gln Ser Gln Ser Ser Arg Glu Ser Pro Pro Gln
                675                 680                 685

Gln Gln Pro Pro Arg Leu Pro Pro Glu Val Glu Ala Gly Gln Arg Leu
                690                 695                 700

Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
                740                 745                 750

Asp Arg Gly Leu Ile Ser Tyr Lys Gly Leu Pro Pro Glu Ala Trp Gln
                755                 760                 765

Glu Glu Cys Pro Ser Asp Ser Glu Glu Asp Glu Gly Arg Gly Glu Arg
                770                 775                 780

Thr Ala Phe Ile Lys Asp Gln Ser Ala Leu
785                 790

(2) INFORMATION FOR SEQ ID NO:3:

(i) SEQUENCE CHARACTERISTICS:
        (A) LENGTH: 4405 base pairs
        (B) TYPE: nucleic acid
        (C) STRANDEDNESS: double (D) TOPOLOGY: unknown (ii) MOLECULE TYPE: DNA (genomic)

(ix) FEATURE:
               (A) NAME/KEY: CDS
               (B) LOCATION: 408..2789

(xi) SEQUENCE DESCRIPTION: SEQ ID NO:3:

```
GAATTCGGAG ATCTACAGGG CTGCCCCCGC CCGCGCCGGA GCTGGAGCCC AGGCCGAGCC       60

CTGCCCTGGT CGCCGGCCGG GCCGAGGCCG CGCCGCCGCG CCTCCCCGCC TCCGCGCCGT      120

GACGCTGCCG CCGGGCGCGG GGACCGCGCC GAGCCCAGGC CCCCGCCGCC GGGCTCTCCG      180

CTCGGCCGAG GGGCGCCCGA GCCGCCGCGG CGGTCGCCTG GAAAAGTTTC CCCGCCAGGG      240

CTCCCCAGGG GTCGGCACTC TTCACCCTCC CGAGCCCTGC CCGTCTCGGC CCCATGCCCC      300

CACCAGTCAG CCCCGGGCCA CAGGCAGTGA GCAGGCACCT GGGAGCCGAG GCCTGTGACC      360

AGGCCAAGGA GACGGGCGCT CCAGGGTCCC AGCCACCTGT CCCCCCC ATG GAG CTG        416
                                                   Met Glu Leu
                                                     1
```

```
AGG CCC TGG TTG CTA TGG GTG GTA GCA GCA ACA GGA ACC TTG GTC CTG       464
Arg Pro Trp Leu Leu Trp Val Val Ala Ala Thr Gly Thr Leu Val Leu
  5                  10                  15

CTA GCA GCT GAT GCT CAG GGC CAG AAG GTC TTC ACC AAC ACG TGG GCT       512
Leu Ala Ala Asp Ala Gln Gly Gln Lys Val Phe Thr Asn Thr Trp Ala
 20                  25                  30                  35

GTG CGC ATC CCT GGA GGC CCA GCG GTG GCC AAC AGT GTG GCA CGG AAG       560
Val Arg Ile Pro Gly Gly Pro Ala Val Ala Asn Ser Val Ala Arg Lys
                 40                  45                  50

CAT GGG TTC CTC AAC CTG GGC CAG ATC TTC GGG GAC TAT TAC CAC TTC       608
His Gly Phe Leu Asn Leu Gly Gln Ile Phe Gly Asp Tyr Tyr His Phe
                 55                  60                  65

TGG CAT CGA GGA GTG ACG AAG CGG TCC CTG TCG CCT CAC CGC CCG CGG       656
Trp His Arg Gly Val Thr Lys Arg Ser Leu Ser Pro His Arg Pro Arg
             70                  75                  80

CAC AGC CGG CTG CAG AGG GAG CCT CAA GTA CAG TGG CTG GAA CAG CAG       704
His Ser Arg Leu Gln Arg Glu Pro Gln Val Gln Trp Leu Glu Gln Gln
         85                  90                  95

GTG GCA AAG CGA CGG ACT AAA CGG GAC GTG TAC CAG GAG CCC ACA GAC       752
Val Ala Lys Arg Arg Thr Lys Arg Asp Val Tyr Gln Glu Pro Thr Asp
100                 105                 110                 115

CCC AAG TTT CCT CAG CAG TGG TAC CTG TCT GGT GTC ACT CAG CGG GAC       800
Pro Lys Phe Pro Gln Gln Trp Tyr Leu Ser Gly Val Thr Gln Arg Asp
                120                 125                 130

CTG AAT GTG AAG GCG GCC TGG GCG CAG GGC TAC ACA GGG CAC GGC ATT       848
Leu Asn Val Lys Ala Ala Trp Ala Gln Gly Tyr Thr Gly His Gly Ile
                135                 140                 145

GTG GTC TCC ATT CTG GAC GAT GGC ATC GAG AAG AAC CAC CCG GAC TTG       896
Val Val Ser Ile Leu Asp Asp Gly Ile Glu Lys Asn His Pro Asp Leu
                150                 155                 160

GCA GGC AAT TAT GAT CCT GGG GCC AGT TTT GAT GTC AAT GAC CAG GAC       944
Ala Gly Asn Tyr Asp Pro Gly Ala Ser Phe Asp Val Asn Asp Gln Asp
165                 170                 175

CCT GAC CCC CAG CCT CGG TAC ACA CAG ATG AAT GAC AAC AGG CAC GGC       992
Pro Asp Pro Gln Pro Arg Tyr Thr Gln Met Asn Asp Asn Arg His Gly
180                 185                 190                 195

ACA CGG TGT GCG GGG GAA GTG GCT GCG GTG GCC AAC AAC GGT GTC TGT      1040
Thr Arg Cys Ala Gly Glu Val Ala Ala Val Ala Asn Asn Gly Val Cys
                200                 205                 210

GGT GTA GGT GTG GCC TAC AAC GCC CGC ATT GGA GGG GTG CGC ATG CTG      1088
Gly Val Gly Val Ala Tyr Asn Ala Arg Ile Gly Gly Val Arg Met Leu
```

-continued

```
              215                 220                 225
GAT GGC GAG GTG ACA GAT GCA GTG GAG GCA CGC TCG CTG GGC CTG AAC    1136
Asp Gly Glu Val Thr Asp Ala Val Glu Ala Arg Ser Leu Gly Leu Asn
            230                 235                 240

CCC AAC CAC ATC CAC ATC TAC AGT GCC AGC TGG GGC CCC GAG GAT GAC    1184
Pro Asn His Ile His Ile Tyr Ser Ala Ser Trp Gly Pro Glu Asp Asp
            245                 250                 255

GGC AAG ACA GTG GAT GGG CCA GCC CGC CTC GCC GAG GAG GCC TTC TTC    1232
Gly Lys Thr Val Asp Gly Pro Ala Arg Leu Ala Glu Glu Ala Phe Phe
260                 265                 270                 275

CGT GGG GTT AGC CAG GGC CGA GGG GGG CTG GGC TCC ATC TTT GTC TGG    1280
Arg Gly Val Ser Gln Gly Arg Gly Gly Leu Gly Ser Ile Phe Val Trp
                280                 285                 290

GCC TCG GGG AAC GGG GGC CGG GAA CAT GAC AGC TGC AAC TGC GAC GGC    1328
Ala Ser Gly Asn Gly Gly Arg Glu His Asp Ser Cys Asn Cys Asp Gly
            295                 300                 305

TAC ACC AAC AGT ATC TAC ACG CTG TCC ATC AGC AGC GCC ACG CAG TTT    1376
Tyr Thr Asn Ser Ile Tyr Thr Leu Ser Ile Ser Ser Ala Thr Gln Phe
            310                 315                 320

GGC AAC GTG CCG TGG TAC AGC GAG GCC TGC TCG TCC ACA CTG GCC ACG    1424
Gly Asn Val Pro Trp Tyr Ser Glu Ala Cys Ser Ser Thr Leu Ala Thr
325                 330                 335

ACC TAC AGC AGT GGC AAC CAG AAT GAG AAG CAG ATC GTG ACG ACT GAC    1472
Thr Tyr Ser Ser Gly Asn Gln Asn Glu Lys Gln Ile Val Thr Thr Asp
340                 345                 350                 355

TTG CGG CAG AAG TGC ACG GAG TCT CAC ACG GGC ACC TCA GCC TCT GCC    1520
Leu Arg Gln Lys Cys Thr Glu Ser His Thr Gly Thr Ser Ala Ser Ala
                360                 365                 370

CCC TTA GCA GCC GGC ATC ATT GCT CTC ACC CTG GAG GCC AAT AAG AAC    1568
Pro Leu Ala Ala Gly Ile Ile Ala Leu Thr Leu Glu Ala Asn Lys Asn
            375                 380                 385

CTC ACA TGG CGG GAC ATG CAA CAC CTG GTG GTA CAG ACC TCG AAG CCA    1616
Leu Thr Trp Arg Asp Met Gln His Leu Val Val Gln Thr Ser Lys Pro
            390                 395                 400

GCC CAC CTC AAT GCC AAC GAC TGG GCC ACC AAT GGT GTG GGC CGG AAA    1664
Ala His Leu Asn Ala Asn Asp Trp Ala Thr Asn Gly Val Gly Arg Lys
            405                 410                 415

GTG AGC CAC TCA TAT GGC TAC GGG CTT TTG GAC GCA GGC GCC ATG GTG    1712
Val Ser His Ser Tyr Gly Tyr Gly Leu Leu Asp Ala Gly Ala Met Val
420                 425                 430                 435

GCC CTG GCC CAG AAT TGG ACC ACA GTG GCC CCC CAG CGG AAG TGC ATC    1760
Ala Leu Ala Gln Asn Trp Thr Thr Val Ala Pro Gln Arg Lys Cys Ile
                440                 445                 450

ATC GAC ATC CTC ACC GAG CCC AAA GAC ATC GGG AAA CGG CTC GAG GTG    1808
Ile Asp Ile Leu Thr Glu Pro Lys Asp Ile Gly Lys Arg Leu Glu Val
            455                 460                 465

CGG AAG ACC GTG ACC GCG TGC CTG GGC GAG CCC AAC CAC ATC ACT CGG    1856
Arg Lys Thr Val Thr Ala Cys Leu Gly Glu Pro Asn His Ile Thr Arg
            470                 475                 480

CTG GAG CAC GCT CAG GCG CGG CTC ACC CTG TCC TAT AAT CGC CGT GGC    1904
Leu Glu His Ala Gln Ala Arg Leu Thr Leu Ser Tyr Asn Arg Arg Gly
            485                 490                 495

GAC CTG GCC ATC CAC CTG GTC AGC CCC ATG GGC ACC CGC TCC ACC CTG    1952
Asp Leu Ala Ile His Leu Val Ser Pro Met Gly Thr Arg Ser Thr Leu
500                 505                 510                 515

CTG GCA GCC AGG CCA CAT GAC TAC TCC GCA GAT GGG TTT AAT GAC TGG    2000
Leu Ala Ala Arg Pro His Asp Tyr Ser Ala Asp Gly Phe Asn Asp Trp
            520                 525                 530

GCC TTC ATG ACA ACT CAT TCC TGG GAT GAG GAT CCC TCT GGC GAG TGG    2048
Ala Phe Met Thr Thr His Ser Trp Asp Glu Asp Pro Ser Gly Glu Trp
```

-continued

```
                    535                  540                 545
GTC CTA GAG ATT GAA AAC ACC AGC GAA GCC AAC AAC TAT GGG ACG CTG      2096
Val Leu Glu Ile Glu Asn Thr Ser Glu Ala Asn Asn Tyr Gly Thr Leu
            550                 555                 560

ACC AAG TTC ACC CTC GTA CTC TAT GGC ACC GCC CCT GAG GGG CTG CCC      2144
Thr Lys Phe Thr Leu Val Leu Tyr Gly Thr Ala Pro Glu Gly Leu Pro
        565                 570                 575

GTA CCT CCA GAA AGC AGT GGC TGC AAG ACC CTC ACG TCC AGT CAG GCC      2192
Val Pro Pro Glu Ser Ser Gly Cys Lys Thr Leu Thr Ser Ser Gln Ala
580                 585                 590                 595

TGT GTG GTG TGC GAG GAA GGC TTC TCC CTG CAC CAG AAG AGC TGT GTC      2240
Cys Val Val Cys Glu Glu Gly Phe Ser Leu His Gln Lys Ser Cys Val
                600                 605                 610

CAG CAC TGC CCT CCA GGC TTC GCC CCC CAA GTC CTC GAT ACG CAC TAT      2288
Gln His Cys Pro Pro Gly Phe Ala Pro Gln Val Leu Asp Thr His Tyr
            615                 620                 625

AGC ACC GAG AAT GAC GTG GAG ACC ATC CGG GCC AGC GTC TGC GCC CCC      2336
Ser Thr Glu Asn Asp Val Glu Thr Ile Arg Ala Ser Val Cys Ala Pro
        630                 635                 640

TGC CAC GCC TCA TGT GCC ACA TGC CAG GGG CCG GCC CTG ACA GAC TGC      2384
Cys His Ala Ser Cys Ala Thr Cys Gln Gly Pro Ala Leu Thr Asp Cys
645                 650                 655

CTC AGC TGC CCC AGC CAC GCC TCC TTG GAC CCT GTG GAG CAG ACT TGC      2432
Leu Ser Cys Pro Ser His Ala Ser Leu Asp Pro Val Glu Gln Thr Cys
660                 665                 670                 675

TCC CGG CAA AGC CAG AGC AGC CGA GAG TCC CCG CCA CAG CAG CAG CCA      2480
Ser Arg Gln Ser Gln Ser Ser Arg Glu Ser Pro Pro Gln Gln Gln Pro
                680                 685                 690

CCT CGG CTG CCC CCG GAG GTG GAG GCG GGG CAA CGG CTG CGG GCA GGG      2528
Pro Arg Leu Pro Pro Glu Val Glu Ala Gly Gln Arg Leu Arg Ala Gly
            695                 700                 705

CTG CTG CCC TCA CAC CTG CCT GAG GTG GTG GCC GGC CTC AGC TGC GCC      2576
Leu Leu Pro Ser His Leu Pro Glu Val Val Ala Gly Leu Ser Cys Ala
        710                 715                 720

TTC ATC GTG CTG GTC TTC GTC ACT GTC TTC CTG GTC CTG CAG CTG CGC      2624
Phe Ile Val Leu Val Phe Val Thr Val Phe Leu Val Leu Gln Leu Arg
    725                 730                 735

TCT GGC TTT AGT TTT CGG GGG GTG AAG GTG TAC ACC ATG GAC CGT GGC      2672
Ser Gly Phe Ser Phe Arg Gly Val Lys Val Tyr Thr Met Asp Arg Gly
740                 745                 750                 755

CTC ATC TCC TAC AAG GGG CTG CCC CCT GAA GCC TGG CAG GAG GAG TGC      2720
Leu Ile Ser Tyr Lys Gly Leu Pro Pro Glu Ala Trp Gln Glu Glu Cys
                760                 765                 770

CCG TCT GAC TCA GAA GAG GAC GAG GGC CGG GGC GAG AGG ACC GCC TTT      2768
Pro Ser Asp Ser Glu Glu Asp Glu Gly Arg Gly Glu Arg Thr Ala Phe
            775                 780                 785

ATC AAA GAC CAG AGC GCC CTC TGATGAGCCC ACTGCCCACC CCCTCAAGCC         2819
Ile Lys Asp Gln Ser Ala Leu
        790

AATCCCCTCC TTGGGCACTT TTTAATTCAC CAAAGTATTT TTTTATCTTG GGACTGGGTT    2879

TGGACCCCAG CTGGGAGGCA AGAGGGGTGG AGACTGTTTC CCATCCTACC CTCGGGCCCA    2939

CCTGGCCACC TGAGGTGGGC CCAGGACCAG CTGGGGCGTG GGGAGGGCCG TACCCCACCC    2999

TCAGCACCCC TTCCATGTGG AGAAAGGAGT GAAACCTTTA GGGCAGCTTG CCCCGGCCCC    3059

GGCCCCAGCC AGAGTTCCTG CGGAGTGAAG AGGGGCAGCC CTTGCTTGTT GGGATTCCTG    3119

ACCCAGGCCG CAGCTCTTGC CCTTCCCTGT CCCTCTAAAG CAATAATGGT CCCATCCAGG    3179

CAGTCGGGGG CTGGCCTAGG AGATATCTGA GGGAGGAGGC CACCTCTCCA AGGGCTTCTG    3239
```

```
CACCCTCCAC CCTGTCCCCC AGCTCTGGTG AGTCTTGGCG GCAGCAGCCA TCATAGGAAG    3299

GGACCAAGGC AAGGCAGGTG CCTCCAGGTG TGCACGTGGC ATGTGGCCTG TGGCCTGTGT    3359

CCCATGACCC ACCCCTGTGC TCCGTGCCTC CACCACCACT GGCCACCAGG CTGGCGCAGC    3419

CAAGGCCGAA GCTCTGGCTG AACCCTGTGC TGGTGTCCTG ACCACCCTCC CCTCTCTTGC    3479

ACCCGCCTCT CCCGTCAGGG CCCAAGTCCC TGTTTTCTGA GCCCGGGCTG CCTGGGCTGT    3539

TGGCACTCAC AGACCTGGAG CCCCTGGGTG GGTGGTGGGG AGGGGCGCTG GCCCAGCCGG    3599

CCTCTCTGGC CTCCCACCCG ATGCTGCTTT CCCCTGTGGG GATCTCAGGG GCTGTTTGAG    3659

GATATATTTT CACTTTGTGA TTATTTCACT TTAGATGCTG ATGATTTGTT TTTGTATTTT    3719

TAATGGGGGT AGCAGCTGGA CTACCCACGT TCTCACACCC ACCGTCCGCC CTGCTCCTCC    3779

CTGGCTGCCC TGGCCCTGAG GTGTGGGGGC TGCAGCATGT TGCTGAGGAG TGAGGAATAG    3839

TTGAGCCCCA AGTCCTGAAG AGGCGGGCCA GCCAGGCGGG CTCAAGGAAA GGGGGTCCCA    3899

GTGGGAGGGG CAGGCTGACA TCTGTGTTTC AAGTGGGGCT CGCCATGCCG GGGGTTCATA    3959

GGTCACTGGC TCTCCAAGTG CCAGAGGTGG GCAGGTGGTG GCACTGAGCC CCCCCAACAC    4019

TGTGCCCTGG TGGAGAAAGC ACTGACCTGT CATGCCCCCC TCAAACCTCC TCTTCTGACG    4079

TGCCTTTTGC ACCCCTCCCA TTAGGACAAT CAGTCCCCTC CCATCTGGGA GTCCCCTTTT    4139

CTTTTCTACC CTAGCCATTC CTGGTACCCA GCCATCTGCC CAGGGGTGCC CCCTCCTCTC    4199

CCATCCCCCT GCCCTCGTGG CCAGCCCGGC TGGTTTTGTA AGATACTGGG TTGGTGCACA    4259

GTGATTTTTT TCTTGTAATT TAAACAGGCC CAGCATTGCT GGTTCTATTT AATGGACATG    4319

AGATAATGTT AGAGGTTTTA AAGTGATTAA ACGTGCAGAC TATGCAAACC AAAAAAAAAA    4379

AAAAAAACCG TCGACAAAGC GGCCGC                                        4405
```

(2) INFORMATION FOR SEQ ID NO:4:

(i) SEQUENCE CHARACTERISTICS:
        (A) LENGTH: 794 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Leu Arg Pro Trp Leu Leu Trp Val Val Ala Ala Thr Gly Thr
 1               5                  10                  15

Leu Val Leu Leu Ala Ala Asp Ala Gln Gly Gln Lys Val Phe Thr Asn
                20                  25                  30

Thr Trp Ala Val Arg Ile Pro Gly Gly Pro Ala Val Ala Asn Ser Val
            35                  40                  45

Ala Arg Lys His Gly Phe Leu Asn Leu Gly Gln Ile Phe Gly Asp Tyr
        50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
```

-continued

```
        145                 150                 155                 160
Pro Asp Leu Ala Gly Asn Tyr Asp Pro Gly Ala Ser Phe Asp Val Asn
                    165                 170                 175
Asp Gln Asp Pro Asp Pro Gln Pro Arg Tyr Thr Gln Met Asn Asp Asn
                180                 185                 190
Arg His Gly Thr Arg Cys Ala Gly Glu Val Ala Ala Val Ala Asn Asn
                195                 200                 205
Gly Val Cys Gly Val Gly Val Ala Tyr Asn Ala Arg Ile Gly Gly Val
            210                 215                 220
Arg Met Leu Asp Gly Glu Val Thr Asp Ala Val Glu Ala Arg Ser Leu
225                 230                 235                 240
Gly Leu Asn Pro Asn His Ile His Ile Tyr Ser Ala Ser Trp Gly Pro
                245                 250                 255
Glu Asp Asp Gly Lys Thr Val Asp Gly Pro Ala Arg Leu Ala Glu Glu
                260                 265                 270
Ala Phe Phe Arg Gly Val Ser Gln Gly Arg Gly Gly Leu Gly Ser Ile
            275                 280                 285
Phe Val Trp Ala Ser Gly Asn Gly Gly Arg Glu His Asp Ser Cys Asn
        290                 295                 300
Cys Asp Gly Tyr Thr Asn Ser Ile Tyr Thr Leu Ser Ile Ser Ser Ala
305                 310                 315                 320
Thr Gln Phe Gly Asn Val Pro Trp Tyr Ser Glu Ala Cys Ser Ser Thr
                325                 330                 335
Leu Ala Thr Thr Tyr Ser Ser Gly Asn Gln Asn Glu Lys Gln Ile Val
                340                 345                 350
Thr Thr Asp Leu Arg Gln Lys Cys Thr Glu Ser His Thr Gly Thr Ser
                355                 360                 365
Ala Ser Ala Pro Leu Ala Ala Gly Ile Ile Ala Leu Thr Leu Glu Ala
            370                 375                 380
Asn Lys Asn Leu Thr Trp Arg Asp Met Gln His Leu Val Val Gln Thr
385                 390                 395                 400
Ser Lys Pro Ala His Leu Asn Ala Asn Asp Trp Ala Thr Asn Gly Val
                405                 410                 415
Gly Arg Lys Val Ser His Ser Tyr Gly Tyr Gly Leu Leu Asp Ala Gly
                420                 425                 430
Ala Met Val Ala Leu Ala Gln Asn Trp Thr Thr Val Ala Pro Gln Arg
            435                 440                 445
Lys Cys Ile Ile Asp Ile Leu Thr Glu Pro Lys Asp Ile Gly Lys Arg
        450                 455                 460
Leu Glu Val Arg Lys Thr Val Thr Ala Cys Leu Gly Glu Pro Asn His
465                 470                 475                 480
Ile Thr Arg Leu Glu His Ala Gln Ala Arg Leu Thr Leu Ser Tyr Asn
                485                 490                 495
Arg Arg Gly Asp Leu Ala Ile His Leu Val Ser Pro Met Gly Thr Arg
                500                 505                 510
Ser Thr Leu Leu Ala Ala Arg Pro His Asp Tyr Ser Ala Asp Gly Phe
            515                 520                 525
Asn Asp Trp Ala Phe Met Thr Thr His Ser Trp Asp Glu Asp Pro Ser
        530                 535                 540
Gly Glu Trp Val Leu Glu Ile Glu Asn Thr Ser Glu Ala Asn Asn Tyr
545                 550                 555                 560
Gly Thr Leu Thr Lys Phe Thr Leu Val Leu Tyr Gly Thr Ala Pro Glu
                565                 570                 575
```

```
Gly Leu Pro Val Pro Pro Glu Ser Ser Gly Cys Lys Thr Leu Thr Ser
            580                 585                 590

Ser Gln Ala Cys Val Val Cys Glu Glu Gly Phe Ser Leu His Gln Lys
        595                 600                 605

Ser Cys Val Gln His Cys Pro Gly Phe Ala Pro Gln Val Leu Asp
    610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
            660                 665                 670

Gln Thr Cys Ser Arg Gln Ser Gln Ser Ser Arg Glu Ser Pro Pro Gln
        675                 680                 685

Gln Gln Pro Pro Arg Leu Pro Pro Glu Val Glu Ala Gly Gln Arg Leu
    690                 695                 700

Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
            740                 745                 750

Asp Arg Gly Leu Ile Ser Tyr Lys Gly Leu Pro Pro Glu Ala Trp Gln
        755                 760                 765

Glu Glu Cys Pro Ser Asp Ser Glu Asp Glu Gly Arg Gly Glu Arg
    770                 775                 780

Thr Ala Phe Ile Lys Asp Gln Ser Ala Leu
785                 790

(2) INFORMATION FOR SEQ ID NO:5:

(i) SEQUENCE CHARACTERISTICS:
          (A) LENGTH: 36 base pairs
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:5:

CCACCTGTCT GATCAATGGA GCTGAGGCCC TGGTTG                              36

(2) INFORMATION FOR SEQ ID NO:6:

(i) SEQUENCE CHARACTERISTICS:
          (A) LENGTH: 36 base pairs
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:6:

GAGGCCTGAT CACTACTCAG CCAGGTGTGA GGGCAT                              36

(2) INFORMATION FOR SEQ ID NO:7:

(i) SEQUENCE CHARACTERISTICS:
          (A) LENGTH: 36 base pairs
          (B) TYPE: nucleic acid
          (C) STRANDEDNESS: unknown
          (D) TOPOLOGY: unknown
```

-continued (ii) MOLECULE TYPE: DNA (genomic)

(xi) SEQUENCE DESCRIPTION: SEQ ID NO:7:

GCAGCCTGAT CACTATGGAG GTACGGGCAG CCCCTC                36